United States Patent
Hei et al.

(10) Patent No.: US 6,962,714 B2
(45) Date of Patent: Nov. 8, 2005

(54) CRITICAL FLUID ANTIMICROBIAL COMPOSITIONS AND THEIR USE AND GENERATION

(75) Inventors: Robert D. P. Hei, Baldwin, WI (US); Keith E. Olson, Apple Valley, MN (US); Robert J. Ryther, St. Paul, MN (US); Richard K. Staub, Lakeville, MN (US)

(73) Assignee: Ecolab, Inc., St. Paul, MN (US)

( * ) Notice: Subject to any disclaimer, the term of this patent is extended or adjusted under 35 U.S.C. 154(b) by 0 days.

(21) Appl. No.: 10/213,603

(22) Filed: Aug. 6, 2002

(65) Prior Publication Data

US 2004/0033269 A1 Feb. 19, 2004

(51) Int. Cl.⁷ .................. A01N 25/02; A01N 25/22; A01N 37/02; A01N 59/08
(52) U.S. Cl. .................. 424/405; 424/613; 424/618; 424/661; 424/662; 424/663; 424/667; 424/668; 424/669; 424/673; 424/723; 514/159; 514/389; 514/557; 514/558; 514/560; 514/568; 514/576; 514/731
(58) Field of Search .................. 424/405, 406, 424/616, 700, 613, 661–681, 688, 689, 723; 574/557–560, 159–164, 389, 731 568, 576

(56) References Cited

U.S. PATENT DOCUMENTS

| | | |
|---|---|---|
| 4,683,618 A | 8/1987 | O'Brien |
| 5,254,735 A | 10/1993 | Smith et al. |
| 5,306,350 A | 4/1994 | Hoy et al. |
| 5,344,493 A | 9/1994 | Jackson |
| 5,658,595 A | 8/1997 | Van Os |
| 5,833,935 A | 11/1998 | Malchesky |
| 5,866,005 A | 2/1999 | DeSimone et al. |
| 5,955,415 A | 9/1999 | Gutierrez et al. |
| 5,977,403 A * | 11/1999 | Byers .................. 562/6 |
| 5,996,155 A | 12/1999 | Chao et al. |
| 6,099,587 A | 8/2000 | Scialla et al. |

FOREIGN PATENT DOCUMENTS

WO    99/58892    * 11/1999

OTHER PUBLICATIONS

Lee et al., "Water–in–Carbon Dioxide Emulsions: Formation and Stability", *Langmuir*, vol. 15, No. 20, pp. 6781–6791 (1999).

* cited by examiner

Primary Examiner—Neil S. Levy
(74) Attorney, Agent, or Firm—Merchant & Gould P.C.

(57) ABSTRACT

The present invention relates to antimicrobial compositions including a critical, near critical, or supercritical (densified) fluid and an antimicrobial agent, to methods of forming these compositions, and to methods employing these compositions. An antimicrobial agent can be generated in the presence of a densified fluid, for example, by reacting an oxidizing agent with a precursor to the antimicrobial agent.

16 Claims, 1 Drawing Sheet

CRITICAL FLUID ANTIMICROBIAL COMPOSITIONS AND THEIR USE AND GENERATION

FIELD OF THE INVENTION

The present invention relates to antimicrobial compositions including a critical, near critical, or supercritical (densified) fluid and an antimicrobial agent, to methods of generating these compositions, and to methods employing these compositions. An antimicrobial agent can be generated in the presence of a densified fluid, for example, by reacting an oxidizing agent with a precursor to the antimicrobial agent.

BACKGROUND OF THE INVENTION

Many antimicrobial agents are applied as solutions in water or another solvent. Application of such antimicrobial solutions results in wetting of the object treated. Certain antimicrobial agents are gases under ambient conditions. Such antimicrobial agents will typically not wet an object, they are difficult to retain on an object, and they can readily spread and pose toxicity problems.

Supercritical fluids have characteristics of both gases and liquids, but they have never been successfully used for applying antimicrobial agents. Characteristics of supercritical fluids have been documented in several editions of the CRC Handbook of Chemistry and Physics (e.g. pages F-62 to F-64 of the 67th edition, 1986–1987; or pages F66–F67 of the 64th edition, 1983–1984, both published by the CRC Press, Inc., Boca Raton, Fla.).

Supercritical fluids have been used as a medium for synthesis for chromatography of compounds. For example, supercritical carbon dioxide has been used as a reaction medium for alkylation reactions, polymerization reactions, and for complete oxidation of undesired contaminants to carbon dioxide, carbon monoxide and water. Another common application for supercritical fluids is in the extraction of desired compounds from liquid and solid substrates. For example, commercial supercritical extraction chromatography (SFC) uses the extraction capability of the supercritical fluid to isolate compounds, from various substrates, for analytical analysis. Commercially many applications for extraction of colorants, flavorings, and fragrances are known and, on a large industrial scale, caffeine is extracted from coffee and tea. Supercritical fluids have not been employed for effective generation of active antimicrobial agents.

Accordingly, a substantial need exists for improved methods for generating and/or applying antimicrobial agents employing near critical, critical, or supercritical fluids.

SUMMARY OF THE INVENTION

The present invention relates to antimicrobial compositions including a critical, near critical, or supercritical (densified) fluid and an antimicrobial agent, to methods for generating these compositions, and to methods employing these compositions. An antimicrobial agent can be generated in the presence of a densified fluid, for example, by reacting an oxidizing agent with a precursor to the antimicrobial agent.

In an embodiment, the antimicrobial composition of the invention includes a densified fluid and an antimicrobial agent. The densified fluid can be a near critical, critical, supercritical fluid, or another type of fluid with properties of a supercritical fluid. Preferred fluids include carbon dioxide, water, xenon, argon, krypton, ammonia, methane, ethane, propane, propylene, ethylene, methanol, isopropanol, nitrous oxide, sulfur dioxide, toluene, p-xylene, cyclohexane, chlorodifluoromethane, chlorotrifluoromethane, trichlorofluoromethane, perfluoropropane, or a mixture thereof. The antimicrobial agent can include carboxylic acid and/or ester antimicrobial agent, inorganic acid antimicrobial agent, sulfonic acid antimicrobial agent, halogen or halogen compound antimicrobial agent, active oxygen antimicrobial agent, phenolic antimicrobial agent, quaternary ammonium antimicrobial agent, and the like, or a combination thereof. The antimicrobial composition can also include other ingredients, such as a carrier or solvent, co-solvent, co-pressurizing gas, food additive or substance ingredient (e.g., preservative, antioxidant, flavoring agent), buffering agent, fragrance, surfactant, acidulant, alkalinity source, oxidizing agent, or mixture thereof. A preferred antimicrobial composition includes densified carbon dioxide, peroxyacetic acid, hydrogen peroxide, acetic acid, and, optionally, peroxyoctanoic acid and octanoic acid.

The invention also includes a method for applying an antimicrobial agent to an object with or from a densified fluid. This method includes venting at the object a vessel containing densified fluid and antimicrobial agent. Venting can release a composition in which the antimicrobial agent and other components of the composition are evenly distributed in the fluid. Alternatively, venting can strip antimicrobial agent from an antimicrobial composition and release it with the fluid. The object can be any of a variety of objects in need of antimicrobial treatment, such as a food product.

The invention also includes a method for making an antimicrobial composition employing a densified fluid. This method includes reacting an oxidizable substrate with an oxidizing agent in a medium comprising a densified fluid to form an antimicrobial composition. This reaction is typically carried out in a vessel suitable for containing a densified fluid. Reacting can include adding to the vessel the oxidizable substrate and the oxidizing agent, and adding fluid to the vessel to form the densified fluid. Reacting can be conducted at conditions of temperature and pressure sufficient to maintain a densified fluid. For example, a densified carbon dioxide system would operate in a temperature range of about −77° C. to about 100° C. The pressure can be about 14.7 psi to about 10,000 psi. Preferred oxidizable substrates include carboxylic acids.

DETAILED DESCRIPTION OF THE INVENTION

Definitions

Figure 1:
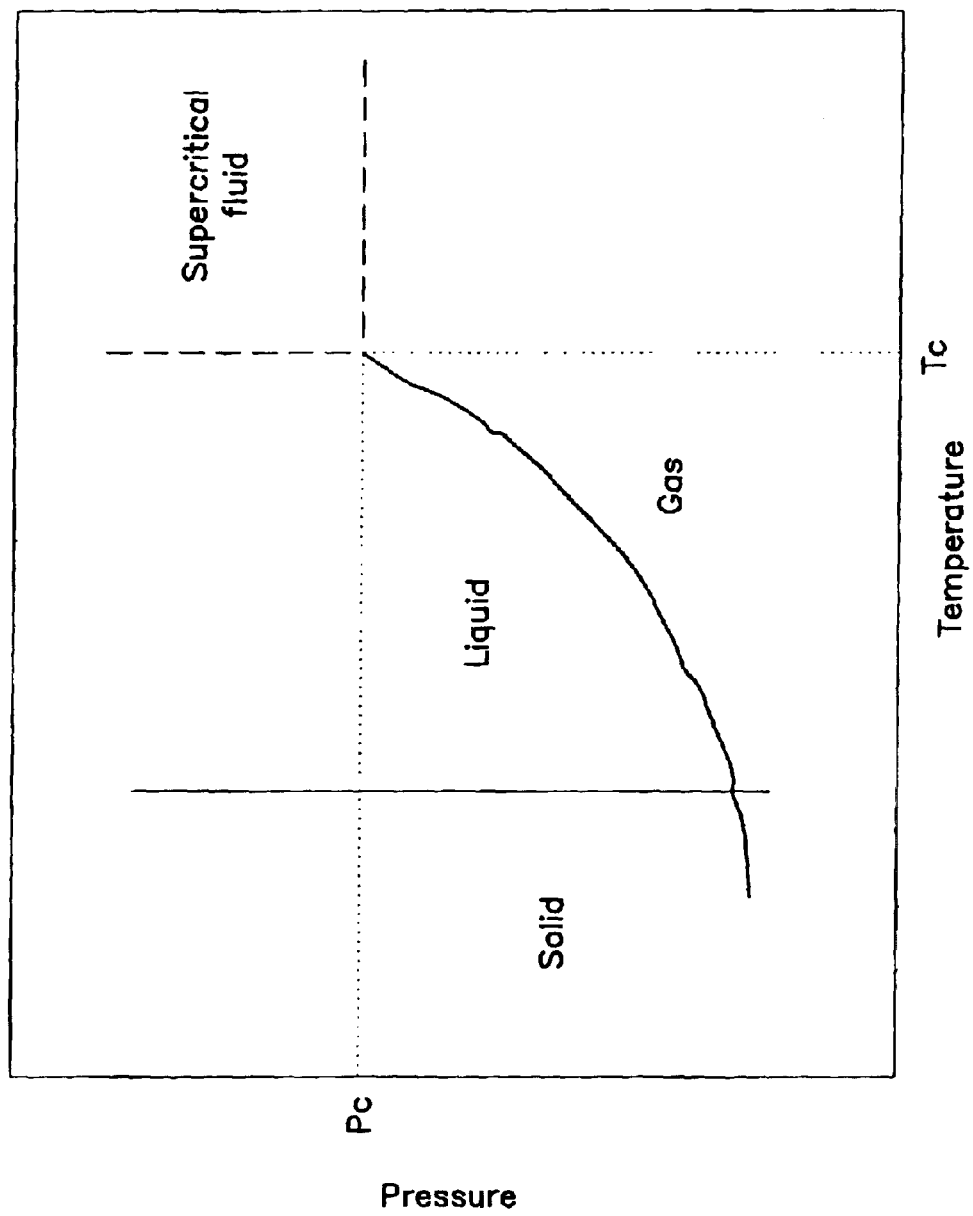
FIG. 1 illustrates a pressure temperature phase diagram of a model material that can have near critical, critical and supercritical properties.

As used herein, the phrase "densified fluid" refers to a fluid in a critical, subcritical, near critical, or supercritical state. The fluid is generally a gas at standard conditions of one atmosphere pressure and 0° C.

As used herein, the phrase "supercritical fluid" refers to a dense gas that is maintained above its critical point—the condition defined by the critical temperature, $T_c$, and critical pressure, $P_c$, of the substance. The critical point of a pure substance can be represented by the apex of the vapor/liquid equilibrium curve. Advantageously, in the supercritical region, high compressibility of the fluid allows adjusting properties of the solutions over a wide range, typically by making modest changes in the pressure of the system. As used herein, the phrase "critical point" refers to the transition point at which the liquid and gaseous states of a substance merge into each other and represents the combination of the critical temperature and critical pressure for a substance. The critical pressure is a pressure just sufficient to cause the appearance of two phases at the critical temperature. Critical temperatures and pressures have been reported for numerous organic and inorganic compounds and several elements. Supercritical fluids are typically less viscous and diffuse more readily than liquids. Preferably a densified fluid is at, above, or slightly below its critical point; and minimally a densified fluid is liquefied.

As used herein, the terms "near critical" fluid or "subcritical" fluid refer to a fluid material that is typically below the critical temperature of a supercritical fluid, but remains in a fluid state and denser than a typical gas due to the effects of pressure on the fluid. Preferably a subcritical or near critical fluid is at a temperature and/or pressure just below its critical point. For example, a subcritical or near critical fluid can be below its critical temperature but above its critical pressure, below its critical pressure but above its critical temperature, or below both its critical temperature and pressure. The terms near critical and subcritical do not refer to materials in their ordinary gaseous or liquid state. Near critical or sub critical fluids require a temperature of at least about 0.5 the critical temperature ($T_c$), preferably at least about 0.7 $T_c$ and/or a pressure of at least about 0.6 the critical pressure ($P_c$), preferably at least about 0.7 $P_c$, more preferably at least about 0.8 $P_c$. Suitable combinations of critical pressure and temperature include about 0.6–10 $P_c$ and/or 0.5–10 $T_c$, about 0.7–4 $P_c$ and/or about 0.7–5 $T_c$, or about 0.8–3 $P_c$ and/or 0.9–3 $T_c$. The present invention can also include these quantities not modified by about.

As used herein, the term "non-critical" refers to a composition without the special properties of a near critical, critical, or supercritical fluid. A non-critical substance is typically a normal gas, liquid, or solid.

As used herein, "supercritical fluid carbon dioxide" refers to carbon dioxide that is at or above its critical temperature of 31° C. and its critical pressure of 71 atmospheres, and which cannot be condensed into a liquid phase despite the addition of further pressure.

For the purpose of this patent application, successful reduction of microorganisms is achieved when the populations of microorganisms are reduced by at least about 0.3–1 $\log_{10}$. In this application, such a population reduction is the minimum acceptable for the processes. Any increased reduction in population of microorganisms is an added benefit that provides higher levels of protection.

As used herein, the term "microorganisms" refers to any noncellular or unicellular (including colonial) organism. Microorganisms include all prokaryotes. Microorganisms include bacteria (including cyanobacteria), lichens, microfungi, protozoa, virinos, viroids, viruses, and some algae. As used herein, the term "microbe" is synonymous with microorganism.

As used herein, the term "object" refers to a something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, and the like. Objects also include a food product (and its surfaces); a body or stream of water or a gas (e.g., an air stream); and surfaces and articles employed in hospitality and industrial sectors.

As used herein, the phrase "food product" includes any food substance that might require treatment with an antimicrobial agent or composition and that is edible with or without further preparation. Food products include meat (e.g. red meat and pork), seafood, poultry, fruits and vegetables, eggs, living eggs, egg products, ready to eat food, wheat, seeds, roots, tubers, leafs, stems, corms, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the phrase "plant product" includes any plant substance or plant-derived substance that might require treatment with an antimicrobial agent or composition. Plant products include seeds, nuts, nut meats, cut flowers, plants or crops grown or stored in a greenhouse, house plants, and the like. Plant products include many animal feeds.

As used herein, a processed fruit or vegetable refers to a fruit or vegetable that has been cut, chopped, sliced, peeled, ground, milled, irradiated, frozen, cooked (e.g., blanched, pasteurized), or homogenized. As used herein a fruit or vegetable that has been washed, colored, waxed, hydrocooled, refrigerated, shelled, or had leaves, stems or husks removed is not processed.

As used herein, the phrase "meat product" refers to all forms of animal flesh, including the carcass, muscle, fat, organs, skin, bones and body fluids and like components that form the animal. Animal flesh includes the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein, the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, sanitizing gels, cooling towers, food processing antimicrobial garment sprays, and non-to-low-aqueous food preparation lubricants, oils, and rinse additives.

As used herein, the phrase "air streams" includes food anti-spoilage air circulation systems. Air streams also include air streams typically encountered in hospital, surgical, infirmity, birthing, mortuary, and clinical diagnosis rooms.

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and hand-wash dip-pans, third-sink rinse waters, and the like. Waters also include domestic and recreational waters such as pools, spas, recreational flumes and water slides, fountains, and the like.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.,), or woven and non-woven surfaces (such as surgical garments, draperies, bed linens, bandages, etc.,), or patient-care equipment (such as respirators, diagnostic equipment, shunts, body scopes, wheel chairs, beds, etc.,), or surgical and diagnostic equipment. Health care surfaces include articles and surfaces employed in animal health care.

As used herein, the term "instrument" refers to the various medical or dental instruments or devices that can benefit from cleaning with a stabilized composition according to the present invention.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, arthoseopes and related equipment, and the like, or combinations thereof.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, weight percent (wt-%), percent by weight, % by weight, and the like are synonyms that refer to the concentration of a substance as the weight of that substance divided by the weight of the composition and multiplied by 100.

As used herein, the terms "mixed" or "mixture" when used relating to "peroxycarboxylic acid composition" or "peroxycarboxylic acids" refer to a composition or mixture including more than one peroxycarboxylic acid, such as a composition or mixture including peroxyacetic acid and peroxyoctanoic acid.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

Methods and Compositions Employing Densified Fluids
Densified Fluids

Near critical, critical, and supercritical (densified) fluids can be used as a reaction medium for the oxidation of materials to form an antimicrobial composition, as a vehicle for an antimicrobial composition, or as a medium for applying an antimicrobial composition. In such reactions, an oxidizable substrate is contacted with an oxidizing agent in the presence of a densified fluid to produce an antimicrobial composition. The antimicrobial composition is preferably maintained under near critical, critical, or supercritical conditions as a concentrate composition. Typically the densified fluid provides a vehicle for the antimicrobial composition. For use, the concentrate composition can be directly applied to a soiled or contaminated object for providing antimicrobial action on the object. For use, the densified fluid composition can be combined with diluent or changed in pressure to apply an antimicrobial composition to the object. Preferably, employing a densified fluid as a vehicle for an antimicrobial agent allows applying the antimicrobial agent to an object with a high concentration of the antimicrobial agent on the object while the vehicle rapidly evaporates leaving little or no vehicle residue on the object.

A variety of densified fluids can be employed in the compositions and methods of the present invention. Preferably, a suitable densified fluid either dissolves, incorporates, or otherwise carries an antimicrobial agent employed in the present invention. Preferably, a suitable densified fluid strips an antimicrobial agent from one or more materials present in the composition. That is, preferably a preferred densified fluid preferentially solubilizes or carries the antimicrobial agent compared to one or more other materials present in the composition. This results in greater delivery of the antimicrobial agent compared to the other material or materials. Preferably, a suitable densified fluid provides a medium in which to run the reaction of a precursor to the antimicrobial agent with an oxidizing agent to form the antimicrobial agent. Preferably, the compressed fluid has a critical temperature above the ambient temperature for applying the antimicrobial composition.

Fluids (e.g., gasses) suitable for densification include carbon dioxide, nitrous oxide, water, nitrogen, ammonia, xenon, krypton, methane, ethane, ethylene, propane, butane, certain fluoroalkanes (e.g., chlorotrifluoromethane, chlorodifluoromethane, 1,1,1,2-tetrafluoroethane, and monofluoromethane), and the like, or mixtures thereof. Preferred densified fluids include water, nitrous oxide, and carbon dioxide; preferably carbon dioxide.

Above the critical temperature the fluid becomes a supercritical fluid attaining the unique properties of a supercritical fluid that seems to have characteristics of both liquid and gas state. At high pressures above the critical point, the resulting supercritical fluid, or "dense gas", will attain densities approaching those of a liquid. These properties are dependent upon the fluid composition, temperature, and pressure. The compressibility of supercritical fluids is great just above the critical temperature where small changes in pressure result in large changes in the density of the supercritical fluid. The "liquid-like" behavior of a supercritical fluid at higher pressures results in greatly enhanced solubilizing capabilities compared to those of the subcritical compound, with higher diffusion coefficients and an extended useful temperature range compared to liquids. Near-supercritical liquids also demonstrate solubility characteristics and other pertinent properties similar to those of supercritical fluids. The solute may be a liquid at the supercritical temperatures, even though it is a solid at lower temperatures.

One unique property of supercritical fluids is the ability of the material to act as a solvent carrier or medium for a variety of materials. The behavior of supercritical fluids at high pressures creates a solubilizing capacity greater than non-critical materials. A variety of compounds become soluble in supercritical fluids, even at relatively low temperatures when similar materials are not soluble under non-critical conditions.

FIG. 1 illustrates a pressure-temperature phase diagram of a fluid that can have near critical, critical and supercritical properties. In the FIGURE, various phases of the fluid are shown, depending on temperature and pressure. The fluid exists in a gas phase in the area below the critical pressure point (Pc) and below the solid line showing the interface between gas phase and a liquid or solid phase. The fluid exists as a supercritical fluid when the material is above the critical pressure and above the critical temperature. The fluid can exist in a near critical liquid phase below the critical temperature.

Densified near critical, critical, and supercritical fluids have attracted increasing attention in recent years. Supercritical water and supercritical carbon dioxide materials have been in use for many years and are known to be environmentally compatible. The *Concise Encyclopedia of Chemical Technology* (Kirk-Othmer) Fourth Edition, 1999, pp. 1943–1944, discloses a basic discussion of densified near critical and supercritical fluids. The Table below lists critical temperatures and pressures for certain fluids.

| Compound | Boiling Point (° C.) | Critical Temperature (° C.) | Critical Pressure (atm) | Critical Density (g/cm$^3$) |
|---|---|---|---|---|
| $H_2O$ | 100.00 | 374.15 | 218.3 (which is equal to 221 bar and 1705 psi) | 0.172 |
| $CO_2$ | −78.5 | 31.3 | 72.9 (which is equal to 0.513 bar and 1071 psi) | 0.468 |
| $NH_3$ | −33.35 | 117.4 | 112.5 | 0.235 |
| $H_2O$ | −88.56 | 36.5 | 71.7 | 0.45 |
| Methane | −164.00 | −82.1 | 45.8 | 0.2 |
| Ethane | −88.63 | 17.28 | 34.1 | 0.203 |
| Propane | −42.1 | 96.67 | 41.9 | 0.217 |
| Methanol | 64.7 | 240.5 | 78.9 | 0.272 |
| Isopropanol | 82.5 | 235.3 | 47.0 | 0.273 |
| Krypton | −153.2 | −63.8 | 54.3 | 0.091 |
| chlorodifluoromethane | −40.8 | 96.1 | 49.7 | 0.512 |
| 1,1,1,2-tetrafluoroethane | −26.5 | 101.1 | 40.7 | 0.515 |

Preferred densified fluids have viscosity that allows convenient application of the antimicrobial agent, for example, by venting a vessel containing the antimicrobial agent and densified fluid.

Viscosity of the densified fluid is typically less than about 1200 cP, preferably less than about 600 cP, more preferably less than about 400 cP when used above the critical temperature and/or pressure. Preferably, the composition of densified fluid and antimicrobial agent is in the range of about 5 to about 1500 cP, preferably about 20 to about 600 cP, preferably about 30 to about 400 cP. The present invention can also include these quantities or ranges not modified by about.

In a preferred embodiment, the antimicrobial agent and densified fluid are selected so that the antimicrobial agent is compatible with, soluble in, or dispensable through the fluid, particularly upon release their container. Preferably, the antimicrobial agent is soluble in the densified fluid to at least about 0.01% by weight of the total composition, more preferably about 1 wt-%, more preferably about 5 wt-%. The present invention can also include these quantities not modified by about. Preferably the antimicrobial agent is used at the highest effective concentration that results in a single phase liquid material, or an emulsified phase material, with manageable viscosity, particularly during application.

Preferred densified fluids include those that can be employed as a vehicle for an antimicrobial agent and/or a reaction medium for making the antimicrobial agent. Such densified fluids are preferably relatively non-flammable, environmentally compatible, and non-toxic to users. Preferred fluids are environmentally compatible, can be made environmentally compatible by treatment, or can be readily recovered from the use environment. For example, carbon dioxide and water are environmentally compatible. Nitrous oxide can be made environmentally compatible by natural decomposition in the environment, or by heating to thermally decompose it, to form molecular nitrogen and oxygen. Ethane and propane can be made environmentally compatible by incineration to carbon dioxide and water. Ammonia is highly soluble in water and can be removed and recovered from air streams by absorption methods such as an air/water scrubber. Other methods can also be used, such as adsorption or solvent recovery.

Preferred densified fluids include water and carbon dioxide because of the non-toxic, environmentally compatible and non-flammable nature of the resulting materials. Further, nitrous oxide ($N_2O$) can form a useful densified fluid. Mixtures of compressed carbon dioxide and nitrous oxide can be useful because nitrous oxide and carbon dioxide have different polarity and solvent properties. Compressed ammonia has still higher polarity and even relatively small amounts in combination with nitrous oxide may be useful to obtain higher solubility in some compositions.

The densified fluid antimicrobial composition can also include other ingredients, such as another fluid (e.g., water) or gas; a carrier, solvent or cosolvent; a surfactant; an enzyme; an oxidizing agent; a co-pressurizing gas or gases; a food additive or substance (e.g., preservative, antioxidant, flavoring agent); a buffering agent; a fragrance; an acidulant; a source of alkalinity; a bleach; an optical brightener; a rheology modifiers; a softener; a starch, or a mixture thereof. A preferred antimicrobial composition includes densified carbon dioxide, peroxyacetic acid, hydrogen peroxide, acetic acid, and, optionally, peroxyoctanoic acid and octanoic acid.

Supercritical, subcritical, near supercritical, and other dense fluids and solvents that can be employed with such fluids are disclosed in U.S. Pat. No. 5,306,350, issued Apr. 26, 1994 to Hoy et al., which is incorporated herein for such disclosure. Emulsions of water in carbon dioxide and surfactants used in their formation are described in Lee, Jr. et al. Langmuir 15, 6781–6791 (1999), which is incorporated herein by reference for such disclosure.

Densified Carbon Dioxide

Preferred densified fluids for the present methods and compositions include carbon dioxide. For the purposes of the present invention, densified carbon dioxide can be produced and used under a range of conditions, such as at various temperatures and pressures. Temperatures suitable for densified carbon dioxide include temperatures in the range of about −77° C. to about 100° C., preferably about −10° C. to about 60° C., and more preferably about 20° C. to about 50° C. Temperatures suitable for near critical carbon dioxide include temperatures in the range of about 25° C. to about −100° C., preferably about 30° C. to about 60° C., and more preferably about 17° C. to about 50° C. Temperatures suitable for supercritical carbon dioxide include temperatures in the range of about 31° C. to about 100° C., preferably about 31° C. to about 60° C., and most preferably about 31° C. to about 50° C.

Suitable pressures for densified fluid antimicrobial compositions according to the present invention can include about 15 psi to about 10,000 psi, preferably 700 psi to about 7,000 psi and most preferably 800 psi to about 3,000 psi. Pressures suitable for densified carbon dioxide include pressures in the range of about 15 psi to about 10,000 psi, preferably about 700 psi to about 7000 psi, and more preferably about 800 psi to about 3,000 psi. Pressures suitable for near critical carbon dioxide include pressures in the range of about 900 psi to about 10,000 psi, preferably about 1000 psi to about 4000 psi, and more preferably about 1050 psi to about 3000 psi. Pressures suitable for supercritical carbon dioxide include pressures in the range of about 1070 psi to about 10,000 psi, preferably about 1070 psi to about 4000 psi, and most preferably about 1070 psi to about 2000 psi. A preferred densified carbon dioxide system includes pressure exceeding about 700 psi at about 20° C.

Carbon dioxide densified fluid compositions can take the form of, for example, single-phase or multi-phase solutions, emulsions, micro-emulsions, or suspensions. Compositions including a solvent that is miscible with the densified carbon dioxide typically take the form of a single-phase solution. Compositions including a solvent that is not miscible with the densified carbon dioxide typically take the form of a multi-phase solution, an emulsion, a micro-emulsion, or a suspension. Even a single solvent containing different solutes can produce either single- or multi-phase densified carbon dioxide compositions, depending on the solute.

Supercritical and other dense forms of carbon dioxide, and cosolvents, co-surfactants, and other additives that can be employed with these forms of carbon dioxide are disclosed in U.S. Pat. No. 5,866,005, issued Feb. 2, 1999 to DeSimone et al., which is incorporated herein for such disclosure.

Modifiers of Densified Fluid Compositions

Modifiers of densified fluid compositions alter properties of the composition significantly, even in relatively low concentration, advantageously increasing solubility for certain solutes. A preferred modifier increases solubility of a preferred solute, such as an antimicrobial agent by at least about 1.5-fold, preferably at least about 2-fold, preferably at least about 5-fold. Such modifiers include co-solvents, surfactants, and solutes, particularly those that include a $CO_2$ (carbon dioxide)-philic group linked to a $CO_2$-phobic group. One or more modifiers can be included in the compositions of the invention.

A preferred modifier, such as a co-solvent or surfactant, is compatible as an indirect or direct food additive or substance; especially those described in the Code of Federal Regulations (CFR), Title 21—Food and Drugs, parts 170 to 186.

Surfactant Modifiers

Numerous known surfactants can be suitable as modifiers. See, e.g., McCutcheon's Volume 1: Emulsifiers & Detergents (1995 North American Edition) (MC Publishing Co., 175 Rock Road, Glen Rock, N.J. 07452). Surfactants employed as additives in $CO_2$ systems are disclosed in patents U.S. Pat. No. 4,592,348, U.S. Pat. No. 5,676,705, U.S. Pat. No. 5,683,473, U.S. Pat. No. 5,783,082, U.S. Pat. No. 5,858,022, U.S. Pat. No. 5,866,005, and PCT Application WO96/27704, each of which is incorporated herein by reference for such disclosure. Examples of the major surfactant types that can be used as modifiers include: alcohols, alkanolamides, alkanolamines, alkylaryl sulfonates, alkylaryl sulfonic acids, alkylbenzenes, amine acetates, amine oxides, amines, sulfonated amines and amides, betaine derivatives, block polymers, carboxylated alcohol or alkylphenol ethoxylates, carboxylic acids and fatty acids, diphenyl sulfonate derivatives, ethoxylated alcohols, ethoxylated alkylphenols, ethoxylated amines and/or amides, ethoxylated fatty acids, ethoxylated fatty esters and oils, fatty esters, fluorocarbon-based surfactants, glycerol esters, glycol esters, heterocyclic-type products, imidazolines and imidazoline derivatives, isethionates, lanolin-based derivatives, lecithin and lecithin derivatives, alkyl glycosides and glucosamines, lignin and lignin derivatives, maleic or succinic anhydrides, methyl esters, monoglycerides and derivatives, olefin sulfonates, phosphate esters, lecithin and its derivatives, phosphorous organic derivatives, polyethylene glycols, polymeric surfactants (e.g., polysaccharides, acrylic acid, and acrylamide), propoxylated and ethoxylated fatty acids alcohols or alkyl phenols, protein-based surfactants, quaternary surfactants, sarcosine derivatives, silicone-based surfactants, soaps, sorbitan derivatives, sucrose and glucose esters and derivatives, sulfates and sulfonates of oils and fatty acids, sulfates and sulfonates ethoxylated alkylphenols, sulfates of alcohols, sulfates of ethoxylated alcohols, sulfates of fatty esters, sulfonates of benzene, cumene, toluene and xylene, sulfonates of condensed naphthalenes, sulfonates of dodecyl and tridecylbenzenes, sulfonates of naphthalene and alkyl naphthalene, sulfonates of petroleum, sulfosuccinamates, sulfosuccinates and derivatives, taurates, thio and mercapto derivatives, tridecyl and dodecyl benzene sulfonic acids, and the like.

Co-Solvent Modifiers

Preferred co-solvents for use as modifiers include 2-(2-aminoethoxy)ethanol, monoethanolamine, diethanolamine, triethanolamine, amyl acetate, amyl alcohol, butanol, 3-butoxyethyl-2-propanol, butyl acetate, n-butyl propionate, cyclohexanone, diacetone alcohol, diethoxyethanol, diethylene glycol methyl ether, diethylene glycol n-butyl ether, diisobutyl carbinol, diisobutyl ketone, dimethyl heptanol, dipropylene glycol n-butyl ether, dipropylene glycol methyl ether, dipropylene glycol propyl ether, dipropylene glycol tert-butyl ether, ethanol, ethyl acetate, 2-ethylhexanol, ethyl propionate, ethylene glycol butyl ether, ethylene glycol methyl ether acetate, hexanol, isobutanol, isobutyl acetate, isobutyl heptyl ketone, isophorone, isopropanol, isopropyl acetate, methanol, methyl amyl alcohol, methyl n-amyl ketone, 2-methyl-1-butanol, methyl ethyl ketone, methyl isobutyl ketone, 1-pentanol, n-pentyl propionate, 1-propanol, n-propyl acetate, n-propyl propionate, propylene glycol n-butyl ether, propylene glycol ethyl ether, propylene glycol methyl ether, propylene glycol n-propyl ether, tripropylene glycol methyl ether and tripropylene glycol n-butyl ether. Ethylene glycol butyl ether and dipropylene glycol n-butyl ether are more preferred cosolvents. Mixtures of cosolvents can be used if desired.

Commercially available cosolvents (all of which are available from Union Carbide Corp.) include those sold under the trade names: Butoxyethyl PROPASOL™, Butyl CARBITOL™ acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™ Low Gravity, CELLOSOLVE™ acetate, CELLOSOLVE™, Ester EEP™, FILMER IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™, Methyl PROPASOL™ acetate, Methyl PROPASOL™, Propyl CARBITOL™, Propyl CELLOSOLVE™, Propyl DIPROPASOL™ and Propyl PROPASOL™.

Densified Fluid Emulsions

A densified fluid can also form an emulsion with a solvent such as water in the presence of a surfactant. The compositions of the present invention include and the methods of the invention can employ emulsions of a densified fluid including antimicrobial agent. In particular, perfluoroether ammonium carboxylate surfactants can aid formation of emulsions between water and densified carbon dioxide that include up to 70 volume-% water. Without surfactant, carbon dioxide dissolves water only to about 0.1 wt-%. Other densified fluids can form emulsions with water with these and other surfactants. Preferred surfactants for forming emulsions of densified fluids include those containing a fluorine-containing or a siloxane-containing $CO_2$-philic segment. Preferred solvent combinations that form emulsions in the presence of surfactants include hydrocarbons, benzyl alcohol, glycol ethers, flavorants, fragrances. More preferred emulsifiers, surfactants, or solvents for emulsions include those that are allowed as indirect or direct food additive or substance; especially those described in the Code of Federal Regulations, Title 21—Food and Drugs, parts 170 to 186 and 570 to 574.

Solvent for Use with Densified Fluids

A solvent fraction mixed with the densified fluid as part of the densified fluid antimicrobial composition can include any active organic solvent and/or non-aqueous diluent which is at least partially miscible with the fluid and can form a solution, dispersion, or suspension with the densified fluid and the antimicrobial agent. Certain preferred solvents are at least partially miscible with water and can form a single phase of the solvent, water, and the fluid. More preferred solvents include those that are cited in the Code Of Federal Regulations (CFR), Title 21, parts 170–186; i.e., food grade, food derived, food additive, food substance, generally recognized as safe (GRAS), or allowed as flavors or fragrances.

Solvents that can be employed in the present invention include, but are not limited to, $C_{1-16}$ aliphatic and aromatic alcohols and esters such as methanol, ethanol, propanol, isopropanol, butanol, iso-butanol, amyl alcohol, octanol, nonanol, and other aliphatic alcohols, acetamidophenol, acetanilide, acetophenone, [2-acetyl-1-methylpyrrole, benzyl acetate, benzyl alcohol, phenethanol, benzyl benzoate, amyl acetate, methyl acetate, ethyl acetate and other alkyl carboxylic esters; ethers, hydroxyethers, or glycol ether esters including ethers, such as methyl t-butyl ether, dibutyl ether, methyl phenyl ether and other aliphatic or alkyl aromatic ethers; glycol ethers such as ethoxy ethanol, butoxy ethanol, ethoxy 2-propanol, propoxy ethanol, butoxy 2-propanol, benzyloxyethanol, ethylene glycol phenyl ether, DOWANOL EPH™ (commercially available from Dow Chemical Co.), propylene glycol phenyl ether (commercially available as DOWANOL PPH™ from Dow Chemical Co.), butoxy ethanol, propoxy ethanol, hexoxy ethanol, isopropoxy 2-propanol, butoxy 2-propanol, propoxy 2-propanol, tertiary butoxy 2-propanol, ethoxy ethanol, butoxy ethoxy ethanol, propoxy ethoxy ethanol, hexoxy ethoxy ethanol, methoxy ethanol, methoxy 2-propanol, and ethoxy ethoxy ethanol and other glycol ethers; glycol ether esters such as butoxy ethoxy acetate, ethyl 3-ethoxy propionate; essential oils (e.g., benzaldehyde, pinenes (alphas, betas, and the like), terpineols, terpinenes, carvone, cinnamealdehyde, borneol and its esters, citrals, ionenes, jasmine oil, limonene, dipentene, linalool and its esters); dibasic esters such as dimethyl adipate, dimethyl succinate, dimethyl glutarate (often available in a mix; including products available under the trade designations DBE, DBE-3, DBE-4, DBE-5, DBE-6, DBE-9, DBE-IB, and DBE-ME from DuPont Nylon Intermediates and Specialties), dimethyl malonate, diethyl adipate, diethyl succinate, diethyl glutarate, dibutyl succinate, and dibutyl glutarate; dialkyl carbonates such as dimethyl carbonate, diethyl carbonate, dipropyl carbonate, diisopropyl carbonate, and dibutyl carbonate; $C_{1-16}$ protonated carboxylic acids such as 2-ethyl-1-hexanoic acid, butyric acid, octanoic acid, heptanoic acid, nonanoic acid, and decanoic acid; $C_{1-12}$ organic anhydrides such as acetic anhydride, succinic anhydride, phthalic anhydride, maleic anhydride, and alkyl or alkenyl succinic anhydrides; organo-nitriles such as benzonitrile; $C_{3-16}$ organo-phosphates and phosphonates such as tributyl phosphate, tripropyl phosphate, 2-ethyl-1-hexyl phosphate; and phthalate esters such as dibutyl phthalate, diethylhexyl phthalate, and diethyl phthalate. Also included are $C_{4-16}$ lactones and lactams such as n-methyl-2-pyrrolidone, and cyclic ureas such as dimethyl ethylene urea. Mixtures of solvents can be used if desired.

Other solvents which may be employed in the methods and compositions of the present invention include ketones such as acetone, methyl ethyl ketone, methyl isobutyl ketone, mesityl oxide, methyl amyl ketone, cyclohexanone and other aliphatic ketones; aromatic hydrocarbons such as toluene, xylene, and other aromatics or mixtures of aromatic solvents; aliphatic hydrocarbons such as VM&P naphtha and mineral spirits, and other aliphatics or mixtures of aliphatics; nitro alkanes such as 2-nitropropane; fluorinated and other halogenated solvents (e.g., chlorotrifluoromethane, trichlorofluoromethane, perfluoropropane, chlorodifluoromethane, and sulfur hexafluoride); amides (e.g., dimethyl acetamide), and the like.

Antimicrobial Agents

Any of a variety of antimicrobial agents can be made in and/or applied from a composition including a densified fluid. Antimicrobial agents that can be applied from a composition of a densified fluid include any of a variety of non-food or food surface compatible antimicrobial agents. More preferred antimicrobial agents include those that are cited in the Code Of Federal Regulations (CFR), Title 21, parts 170–186. The antimicrobial agent can be dissolved, emulsified, suspended, or dispersed in the densified fluid or in a second diluting gas or solvent phase.

Suitable antimicrobial agents include: carboxylic acids, diacids, or triacids such as acetic acid, formic acid, propionic acid, lactic acid, butyric acid, hexanoic acid, heptanoic acid, octanoic acid, nonanoic acid, decanoic acid, salicylic acid, mandelic acid, malonic acid, succinic acid, adipic acid, glutaric acid, sebacic acid, EDTA and citric acid; inorganic acids such as carbonic acid; carboxylic, esters such as p-hydroxy alkyl benzoates, alkyl cinnamates, alkyl adipates (e.g., dimethyl adipate, diethyl adipate, iso-butyl adipate), alkyl succinates (e.g., methyl succinate, ethyl succinate, iso-butyl succinate), alkyl sebacates (e.g., methyl, or alkyl glutarates; sulfonic acids such as dodecylbenzene sulfonic acid; iodo-compounds or active halogen compounds such as iodine or halogen complexes like alkaline BrCl, or interhalides like IBr, ICl, $ICl_2$, $ICl_4$, or polyhalides like $I_x$ (x=3–9), or acid/metal hypochlorites like HOCl, NaOCl, $CaOCl_2$, or acid/metal hypobromites like HOBr, NaOBr, or chloro- and/or bromo-hydantoins, or chlorine dioxide and sodium chlorite; active oxygen compounds including hydrogen peroxide, or isolated or equilibrium derived isolated peroxy-carboxylic acids (also called peracids or peroxyacids) such as chloroperbenzoic acids, peracetic acid, perheptanoic acid, peroctanoic acid, perdecanoic acid, performic acid, percitric acid, perglycolic acid, perlactic acid, perbenzoic acid, and monoester peracids derived from diacids, mono-ester diacids, or diesters (e.g., such as adipic, succinic, glutaric, sebacic, or malonic acids/esters and mixtures thereof), organic peroxides (including benzoyl hydro-peroxide tert-butyl benzoyl peroxide, and alkyl peroxides), inorganic peroxides (e.g., salts of percarbonates, persulfates, perborates, and the like), and organo-inorganics (e.g., acetyl (or higher hydrocarbon analogues) perborates, acetyl (or higher hydrocarbon analogues) persulfates), ozone, singlet oxygen generators (e.g., paratoluidine blue, methylene blue), and mixtures thereof, or phenolic derivatives such as o-phenyl phenol, o-benzyl-p-chlorophenol, tert-amyl phenol and $C_1$–$C_6$ alkyl hydroxy benzoates, resorcinol, and especially natural product phenolics like pyrogallol, salicylic acid, gallic acid; or quaternary ammonium compounds such as, alkyldimethylbenzyl ammonium chlorides, dialkyldimethyl ammonium chlorides, alkyltrimethyl ammonium chlorides, choline salts; antimicrobial solvents such as benzyl alcohol, hydroxy benzoate esters, dialkyl diesters (e.g., dimethyl adipate, dimethyl glutarate, etc.,), phenylethanol, and the like; and mixtures of such antimicrobial agents in an amount sufficient to provide the desired degree of microbial protection.

In an embodiment, the present antimicrobial composition can include an antimicrobial carboxylic acid such as formic acid, acetic acid, propionic acid, octanoic acid, heptanoic acid, nonanoic acid, decanoic acid, benzoic acid, salicylic acid, and mixtures thereof.

In an embodiment, the present antimicrobial composition can include an antimicrobial solvent such as benzyl alcohol, a dicarboxylic ester (e.g., dialkyl adipate, dialkyl glutarate, dialkyl succinate dialkyl suberate; especially including DBE™, DBE-3™, DBE-6™, DBE-IB™, DBE-ME available from DuPont Nylon Intermediates and Specialties, 1007 Market Street Wilmington, Del. 19898). In an embodiment, the antimicrobial solvent can be used in combination with another antimicrobial agent such as a carboxylic acid, peroxycarboxylic acid, chlorine dioxide, iodine, an interhalide, or a polyhalide. Such combinations can include a carboxylic acid such as acetic acid, lactic acid, glycolic acid, heptanoic acid, octanoic acid, nonanoic acid, decanoic acid, or mixtures thereof, along with a solvent such as a dicarboxylic ester such as dimethyl adipate or dimethyl suberate. In an embodiment, the combination includes a peroxycarboxylic acid such as peracetic acid, performic acid, percarbonic acid, peroctanoic acid, or mixtures thereof, and a solvent such as a dicarboxylic ester, e.g., dimethyl adipate or dimethyl suberate.

In an embodiment, the present antimicrobial composition can include a halogen containing compound such as chlorine dioxide, hypochlorous acid, hypobromous acid, a hypobromite, a hypochlorite, iodine, an interhalide, or a polyhalide; a peroxygen compound such as a peroxy acid (e.g. a peroxycarboxylic acid, a mono-methyl ester peroxycarboxylic acid, etc.,), a perborate or an organic derivative such as peracetyl borate, a persulfate, or the like.

Many of the aforementioned additional antimicrobial agents (e.g., those having about 1–12 carbons or an ionic charge) are mostly soluble in the diluting densified solvent. A second phase (e.g., water), or surfactant, can be included or incorporated (hydrotroped, solvated, admixed, suspended, dissolved, emulsified) to integrate those that would generally be more soluble in this second phase.

Nanoparticle Antimicrobial Agents

Another class of useable antimicrobials includes nano-scale materials such as nano-particles and nano-emulsions. The nano-particles of specific choice include alkali and alkaline earth oxides, hydroxides, halides and sulfides (e.g., CaO, MgO, $MgCl_2$, $Ca(OH)_2$, $Mg(OH)_2$); metal oxides, hydroxides and sulfides (e.g., $TiO_2$, $Fe_2O_3$, $MnO_4$); metal colloids; inorganic nitrides (e.g., BN, $Al_2N_3$), carbides, sulfides, phosphates, borides; oxides, hydroxides and sulfides of silicon, aluminum and boron. The nanomaterial composition can contain combinations or mixtures of nano-materials (e.g., $MgO+Fe_2O_3+Mg(OH)_2$). Furthermore, the nanomaterial compositions can contain oxides, halides, hydroxides, sulfides, nitrides, carbides, phosphates, borides, organic containing species within or on the surface of the nanoparticle in combination (e.g., FeO(OH), MgO(OH), $MnS_2$(O)(OH), MgO(Cl), Ca(O)I).

The surface of a nanoparticle can be coated with or impregnated with inorganic or organic materials or other nanoparticles such as those described above individually or in mixtures (e.g., Na, K, Ag, Fe2O3 coated on the surface of MgO, TiO2 coated on the surface of MnO4, BN within or coated on the surface of MgO, halides adsorbed or coated on the surface of MgO). The nanoparticles can be impregnated or doped with other elements to alter the acidity or basicity of the particle (e.g., doped with Na, K, Fe, V, Al).

The nanomaterials can be in solid, powder, liquid suspension or emulsion, or gel form and can themselves or in combination with coatings be antibacterial, biocidal, virucidal, bacteriostatic, mildewcidal and fungicidal or otherwise reduce, limit or control the presence of pathogens, molds, fungi and allergens.

Preferred nanomaterials include hydroxides and oxides of Mg, Ca, Ti, Zr, Fe, V, Mn, Ni, Cu, Al, Zn. More preferably, hydroxides and oxides of Mg, Ca, Zn, Al, Ti. More preferably hydroxides and oxides of Mg and Ca.

The nanomaterials can be prepared by any method used to prepare nanometer sized particles including, but not limited to, chemical vapor deposition, laser vaporization, template synthesis (dendritic materials), precipitation, aerogel methods, or xerogel methods. Preferably, the nanomaterials employed in the present composition have an average crystallite size up to 80 nm, more preferably up to 20 nm, and most preferable from 1 to 10 nm. The particles have a surface area as determined by BET methods of about 20 $m^2/g$, more preferred from about 50–1200 $m^2/g$, most preferred from about 200–1000 $m^2/g$. It is understood that the above representations serve only as examples for describing the types of nanomaterials that can be employed. It is not intended to limit the types or combinations of nanomaterials.

Antimicrobial Compositions Including Densified Fluids

An inventive antimicrobial composition can include an antimicrobial agent and a densified fluid. Such an antimicrobial composition can also include additional ingredients. Preferred additional ingredients include those that can stabilize the antimicrobial agent, enhance activity of the antimicrobial agent, stabilize the composition, provide useful properties to the composition, or that are employed or produced in generating the antimicrobial agent. Numerous such ingredients are described herein.

In particular, a composition employed for generating and applying a peroxycarboxylic acid antimicrobial agent can include ingredients that stabilize and/or that are employed in generating the peroxycarboxylic acid. Ingredients employed in generating the peroxycarboxylic acid can include carboxylic acid and an oxidizing agent. Preferred oxidizing agents include peroxides, including hydrogen peroxide, organic peroxides (e.g., t-butyl benzoyl peroxide, benzoyl peroxide), inorganic peroxides (e.g., sodium percarbonate, sodium persulfate, sodium perborate), oxygen, ozone, or a mixture of these oxidizing agents. Preferred carboxylic acids include acetic acid, octanoic acid, heptanoic acid, nonanoic acid, glycolic acid, citric acid, and lactic acid; preferably acetic acid and/or octanoic acid. Peroxycarboxylic acids can also be generated from oxidizing agent and a carboxylate ester, a dicarboxylic acid, a monoester dicarboxylic acid, a diester dicarboxylate (e.g., dimethyl adipate, dimethyl succinate, or dimethyl glutarate) a polycarboxylic acid, and the like. In an embodiment, the antimicrobial composition is made from a diester dicarboxylate such as dimethyl adipate, dimethyl succinate, dimethyl glutarate, or dimethyl sebacate. In an embodiment the peroxycarboxylic acid precursor is compatible as an indirect or direct food additive or substance; for example, as described in the Code of Federal Regulations (CFR), Title 21—Food and Drugs, parts 170 to 186.

Other ingredients that can be employed in generating useful peroxycarboxylic acids, and included in the compositions, are described herein below. Ingredients that can stabilize the peroxycarboxylic acid include phosphonate and other stabilizing agents that are also described herein below. In addition, a peroxycarboxylic acid containing composition can include ingredients such as wetting agents, hydrotropes, defoaming agents, pigments or dyes, and the like.

A preferred densified fluid antimicrobial composition that can be employed in the present methods includes densified carbon dioxide, peroxyacetic acid, hydrogen peroxide, acetic acid, peroxyoctanoic acid, and octanoic acid. This can be referred to as a densified fluid mixed peroxycarboxylic acid composition.

In an embodiment, the composition of the invention includes densified carbon dioxide and 0.001 to about 95.0 wt-% acetic acid, 0.005 to about 75 wt-% $H_2O_2$, and 0.001 to about 35 wt-% peroxyacetic acid for each 0.01 to about 50.0 wt-% of carbon dioxide. In a preferred embodiment, the composition of densified fluid and peroxycarboxylic acid antimicrobial agent also includes 0.001 to about 5 wt-% phosphonate stabilizing agent (e.g., Dequest®) and/or 0.001 to about 65.0 wt-% deionized (DI) water for each 1 to about 50.0 wt-% of carbon dioxide.

In an embodiment, the composition of the invention includes densified carbon dioxide and 0.001 to about 95.0 wt-% percarbonic acid and 0.005 to about 75.0 wt-% $H_2O_2$ for each 1 to about 50.0 wt-% of carbon dioxide.

In an embodiment, the composition of the invention includes densified carbon dioxide and 0.001 to about 75.0 wt-% interhalide or polyhalide for each 1 to about 50.0 wt-% of carbon dioxide.

In certain embodiments, the vented composition includes a higher proportion of antimicrobial agent than the densified fluid composition from which it is produced. For example, during venting of the vessel containing the composition of a densified fluid and an antimicrobial agent, the composition can vent the antimicrobial agent preferentially compared to other components of the composition. Although not limiting to the present invention, it is believed that certain antimicrobial agents, such as peroxycarboxylic acids (e.g., peroxyacetic acid) are preferentially dissolved in or carried by the densified fluid and vented from the container. In particular, it has been observed that peroxycarboxylic acids (e.g., peroxyacetic acid) are vented in preference to hydrogen peroxide from a vessel containing densified carbon dioxide.

Making an Antimicrobial Agent in a Densified Fluid

An antimicrobial agent can be made in a densified fluid by contacting or reacting a substrate that can be converted to the antimicrobial agent with an agent that can effect that conversion in the presence of the densified fluid.

In an embodiment, the method for making an antimicrobial composition includes reacting an oxidizable substrate with an oxidizing agent in the presence of a densified fluid to form an antimicrobial composition, and, preferably, containing the antimicrobial composition in a vessel. In an embodiment, reacting includes adding to the vessel the oxidizable substrate and the oxidizing agent, and adding fluid to the vessel to form the densified fluid.

Suitable oxidizable substrates include a carboxylic acid, a carboxylic ester, a dicarboxylic acid, a monoester dicarboxylic acid, a diester dicarboxylate (e.g., dimethyl adipate, dimethyl succinate, dimethyl glutarate, and the like) a polycarboxylic acid, an inorganic substrate (e.g., carbon dioxide, carbonic acid, or the like), a halogen containing compound such as a halide, or the like, or a mixture thereof. Suitable halogens include iodides (e.g., organic or inorganic iodides such as NaI, KI, iodoacetic acid, and the like), bromides (e.g., NaBr, KBr, N-bromosuccinimide, bromosulfamic acid, tribromophenol, and the like), polyhalides (e.g., $I_2$, $I_3^-$, $Br_3^-$, and the like), interhalides (e.g., $ICl^-$, $ICl_2^-$, $ICl_3^-$, $IBr^-$, and the like), chlorites (e.g., sodium chlorite and the like), or the like, or a mixture thereof.

Suitable oxidizing agents include ozone, a peroxide, oxygen, iodine, bromine, chlorine, a chlorite (e.g., sodium chlorite, potassium chlorite), a chlorate (e.g., sodium chlorate), a hypochlorite (e.g., sodium hypochlorite, calcium hypochlorite), fluorine, iodates (e.g., sodium iodate), bromates, or the like, or, if compatible, a mixture thereof. Suitable peroxides include hydrogen peroxide, organic peroxides (e.g., t-butyl benzoyl peroxide, benzoyl peroxide), inorganic peroxides (e.g., percarbonates, persulfates, perborates), or the like, or, if compatible, a mixture thereof.

In an embodiment, the method for making an antimicrobial composition includes acidifying a chlorite (e.g., sodium chlorite) in the presence of a densified fluid to form an antimicrobial composition, and, preferably, containing the antimicrobial composition in a vessel. In an embodiment, reacting includes adding to the vessel the chlorite and the acid, and adding fluid to the vessel to form the densified fluid.

The antimicrobial agent can be formed by contacting or reacting the components that form the antimicrobial agent in the presence of the densified fluid and in a suitable vessel. Preferably the substrate is mixed with an excess of the agent and a densified fluid. This mixing can occur before or after adding the fluid that becomes densified. In an embodiment, the substrate is mixed with the densified fluid and the agent is added over time to this mixture. Other additives such as co-solvents, surfactants, emulsifiers, solvents, and the like can be added at any stage of this process. Mixing can be as simple as adding the oxidizable substrate and oxidizing agent to the vessel and can also include mechanical stirring, fluid or gas circulation or re-circulation, or combinations of these. Typically, adding the densified fluid includes bringing the pressure of the fluid in the vessel to about 0.6–10 $P_c$, preferably about 0.7–4 $P_c$, preferably 0.8–3 $P_c$. Any of these mixtures can be heated and reacted for some time before, during, or after adding the remaining ingredients. Preferably, all the ingredients are mixed before heating. Heating can bring the vessel containing fluid to about 0 to 300° C., preferably to about 10 to 120° C., and preferably to about 15 to 100° C. Heating includes heating the vessel containing fluid to about or greater than about 0.5–10 $T_c$, preferably about 0.7–5 $T_c$, preferably 0.9–3 $T_c$.

Any of the mixtures can be processed for a suitable time period to obtain the antimicrobial agent. Processing can include draining off residual or produced reactants or products, either gaseous or liquid, from the reactant chamber.

Variations on the process outlined above can include utilizing cross- or counter-flow systems which allow extensive-to-transient contact of the supercritical fluid with another liquid, solid, gas, or supercritical fluid which contains the desired antimicrobial agent; e.g., counter-flow densified carbon dioxide with aqueous solutions of peracids, chlorine dioxide, hypochlorite, interhalide, etc., aqueous solutions which, in traversing one another, extract the active ingredient into the densified phase from the aqueous phase.

Any vessel suitable for containing and/or handling a densified fluid can be employed as a reaction vessel. Preferred reaction vessels include pressure vessels such as a supercritical fluid extraction system.

Making Oxyacids in Densified Carbon Dioxide

The efficiency of making peroxygen acid materials can be substantially improved by conducting the reaction between a peracid precursor and a source of active oxygen in a densified, preferably supercritical, carbon dioxide. For example, the equilibrium between the reactants forming the peracid material can be substantially shifted toward production of the peroxygen acid. This substantially increases the value of the process and product. For this process, the carbon dioxide is preferably made a densified fluid at a temperature at least about 0° C., more preferably about 22° C., or greater than about 0.7 Tc, preferably 0.9 to greater than 1.5 Tc, preferably about Tc to about 0.9 to about 1.2 times Tc, and/or the pressure is at least about 700 psi or greater, preferably greater than about 900 psi, preferably greater than about 1070 psi.

While virtually any acid precursor material can be reacted with an oxidizing agent in the presence of supercritical carbon dioxide, the preferred reaction system involves a reaction between a carboxylic acid and hydrogen peroxide to form the corresponding peroxycarboxylic acid. The hydrogen peroxide is commonly supplied in the form of an aqueous solution of hydrogen peroxide in which the hydrogen peroxide is present at about 0.01 to 70 wt-% of the solution.

Preferred carboxylic acids include formic acid, carbonic acid, acetic acid, propionic acid, heptanoic acid, octanoic acid, nonanoic acid, decanoic acid, lactic acid, citric acid, glycolic acid, and mixtures thereof.

Preferred carboxylic acids also include alkyl ester dicarboxylic acids with the formula:

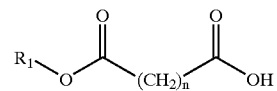

where $R_1$ represents an alkyl group having from 1 to 8 carbons and n is 0 to 6, preferably 1 to 5. The alkyl group can be either straight chain or branched. Preferably, $R_1$ is a methyl, ethyl, propyl (n- or iso-), butyl (n-, iso-, or tert-), n-amyl, n-hexyl, or 2-ethylhexyl group. Preferably, n is 2, 3, or 4. In one preferred embodiment, the composition of the present invention includes a mixture of alkyl ester carboxylic acids in which n is 2, 3, and 4. Such a mixture includes monoesters of adipic, glutaric, and succinic acids. In another preferred embodiment, a majority of the ester carboxylic acid in the composition has n equal to 3. In a preferred embodiment, $R_1$ is a $C_1$–$C_4$ alkyl. In a preferred embodiment, n is 1, 2, 3, or 4. Most preferably, $R_1$ is a $C_1$ alkyl, $C_3$ alkyl, or $C_4$ alkyl, and n is 2, 3 or 4. In another preferred embodiment, $R_1$ is a $C_5$–$C_8$ alkyl, n is 5 or 6.

Other useful precursor materials that can be reacted with an oxidizing agent in the presence of supercritical carbon dioxide include diester dicarboxylates having the formula:

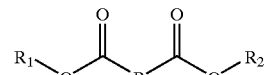

In this formula, $R_1$, $R_2$, and $R_3$ can independently be any of a wide variety of organic groups (e.g. alkyl, linear or cyclic, aromatic or saturated) or substituted organic groups (e.g., with one or more heteroatoms or organic groups). Diester dicarboxylates can be converted to ester peroxycarboxylic acids, for example, by incubating the corresponding diester dicarboxylate with hydrogen peroxide.

Preferred diester dicarboxylates include alkyl diester dicarboxylates having the formula:

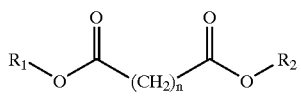

where $R_1$ and $R_2$ represent independently an alkyl group having from 1 to 8 carbons, preferably 1 to 5, and n is 0 to 10, preferably 1 to 8, and most preferably 4–7. The alkyl group can be either straight chain or branched. Preferably, $R_1$ and $R_2$ are independently a methyl, ethyl, propyl (n- or iso-), butyl (n-, iso-, or tert-), n-amyl, n-hexyl, or 2-ethylhexyl group. Preferably, n is 4, 5, 6 or 7. In one preferred embodiment, the composition of the present invention includes a mixture of alkyl diester dicarboxylates in which n is 2, 3, and 4. Such a mixture includes diesters of adipic, glutaric, and succinic acids. In another preferred embodiment, a majority of the alkyl diester dicarboxylates in the composition has n equal to 3 or 4. In yet another preferred embodiment, a majority of the alkyl diester dicarboxylates in the composition has n equal to 5, 6 or 7. In a preferred embodiment, $R_1$ and $R_2$ are independently a $C_1$–$C_8$ alkyl. In a preferred embodiment, n is 1, 2, 3, or 4. Most preferably, $R_1$ and $R_2$ are independently a $C_1$ alkyl, $C_3$ alkyl, $C_4$ alkyl, and n is 2, 3, 4, or 5. In another preferred embodiment, $R_1$ and $R_2$ are independently a $C_5$–$C_8$ alkyl, n is 5 or 6.

Alkyl diester dicarboxylates useful in this invention include all symmetrical and mixed diesters of oxalic acid, malonic acid, succinic acid, glutaric acid, adipic acid, suberic, pimelic, or sebacic acid (or mixtures thereof) with methanol, ethanol, propanol (e.g., n-propanol or isopropanol), butanol (e.g., n-butanol, iso-butanol, or tert-butanol), amyl alcohol (n-pentanol, iso-pentanol, sec-pentanol, or tert-pentanol), hexanol (n-hexanol, iso-hexanol, sec-hexanol, or tert-hexanol), octanol (n-octanol, iso-octanol, sec-octanol, or tert-octanol) or mixtures thereof. Such alkyl diester dicarboxylates especially include dimethyl oxalate, dimethyl malonate, dimethyl succinate, dimethyl glutarate, dimethyl adipate, dimethyl pimelate, dimethyl suberate, and dimethyl sebacate, or a mixture thereof.

The methods and compositions of the present invention can also include diester dicarboxylates known as dibasic esters and available under the trade designations DBE, DBE-3, DBE-4, DBE-5, DBE-6, DBE-9, DBE-IB, and DBE-ME from DuPont Nylon. These "DBEs" include single isolates or mixtures of species such as dimethyl adipate, dimethyl succinate, dimethyl glutarate, and diisobutyl adipate, diisobutyl succinate, and diisobutyl glutarate. Others such as dioctyl sebacate, bis-[2-ethylhexyl] sebacate, diamyl sebacate are commercially available in relatively pure form.

Other suitable acid precursor materials include oxygen containing hydrocarbon species that can readily be oxidized into either a carboxylic acid or a peroxycarboxylic acid material; such as anhydrides and lactones. For example, acid precursor compounds for peracetic acid include ethanol acetaldehyde, acetic acid, acetic anhydride, acetate esters, and other $C_2$ hydrocarbons containing one oxygen atom in the molecule. Suitable oxidizing agents include reactive compounds that can either form hydrogen peroxide in the reaction medium or can directly oxidize the acid precursor to the carboxylic acid or peroxycarboxylic acid material.

Making Polyhalides and Interhalides in Densified Carbon Dioxide

The efficiency of making halogen-based materials can be substantially improved by conducting the reaction between a halogen or halide precursor and a source of oxidant in a densified, preferably supercritical, carbon dioxide. For example, the reaction between the reactants forming the interhalide or polyhalide material can be substantially shifted toward production of the interhalide or polyhalide. This substantially increases the value of the process and product. For this process, the carbon dioxide is preferably made a densified fluid at a temperature at least about 0° C., preferably about 22° C., or greater than about 0.7 Tc, preferably 0.9 to greater than 1.5 Tc, preferably about Tc, preferably about 0.9 to about 1.2 times Tc, and/or the pressure is at least about 700 psi or greater, preferably greater than about 900 psi, and most preferably greater than about 1070 psi.

While virtually any halide or halogen precursor material can be reacted with an oxidizing agent in the presence of supercritical carbon dioxide, the preferred reaction system involves a reaction between a halide (e.g., iodide, bromide, or chloride) and an oxidant (e.g., iodine, bromine, chlorine, iodine monochloride, or iodine monobromide) to form the corresponding interhalide or polyhalide. The oxidant is commonly supplied in the form of an aqueous solution, a neat liquid, or a gas. Preferred halides include iodide, bromide, chloride, and mixtures thereof. Suitable oxidizing agents include iodates, bromates, chlorine, iodine, iodine monochloride, and iodine monobromide. Preferred interhalide or polyhalide products of the reaction include ICl, $ICl_2^-$, $ICl_3^-$, $ICl_4^-$, IBr, $IBr_2^-$, $IBr_3^-$, BrCl, $I_x$ where x is 3 to 9, and mixtures thereof.

Making Chlorine Dioxide in Densified Carbon Dioxide

The efficiency of making halogen-based materials can be substantially improved by conducting the reaction between a chlorine dioxide precursor and a source of oxidant or acid in a densified, preferably supercritical, carbon dioxide. For example, the reaction between the reactants forming the chlorine dioxide can be initiated using a chlorite salt, an inorganic or organic acid, and optionally an oxidant, an iodide, or an iodine salt. For this process, the carbon dioxide is preferably made a densified fluid at a temperature at least about 0° C., preferably about 22° C., or greater than about 0.7 Tc, preferably 0.9 to greater than 1.5 Tc, preferably about Tc to about 0.9 to about 1.2 times Tc, and/or the pressure is at least about 700 psi or greater, preferably greater than about 900 psi, and most preferably greater than about 1070 psi.

Any of several suitable precursor materials can be reacted to form the chlorine dioxide in the presence of supercritical carbon dioxide. In an embodiment, chlorine dioxide is formed from a reaction between a chlorite salt (e.g., sodium or potassium chlorite) and an acidulant. The chlorite salt is commonly supplied in the form of an aqueous solution, or as a neat powder. Suitable acidulants include an inorganic acid (e.g., hydrochloric acid) or an organic acid (e.g., citric acid, salicylic acid, mandelic acid). The reaction forms chlorine dioxide in a densified fluid.

Applying an Antimicrobial Composition Including a Densified Fluid

The present invention also includes methods of applying an antimicrobial agent to an object employing a densified fluid composition of the invention. Typically, the densified fluid dissolves, carries, or otherwise serves as a vehicle for applying the antimicrobial agent. Densified fluid antimicrobial compositions can be applied by any of several methods known to those of skill in the art. Such methods include venting at the food product a vessel containing densified fluid and antimicrobial agent. In an embodiment, the aqueous phase, which can include hydrogen peroxide, is retained in the device. The vented composition includes an effective amount of antimicrobial agent making the densified fluid compositions effective antimicrobial compositions.

Because of the high pressure nature of the densified fluid compositions of the invention, these compositions are typically applied by venting a vessel containing the composition at a soiled or contaminated object through a pressure relief device that is designed to promote rapid efficient coverage of the surface. Devices including such a pressure relief device include sprayers, loggers, foamers, foam pad applicators, brush applicators or any other device that can permit the expansion of the fluid materials from high pressure to ambient pressure while applying the material to the soiled or contaminated surface. Preferred venting or pressure relief methods or devices include atomizers, nozzles (cone, fan, half-circle, atomizing, and the like), spray jets, spray fans, foggers, spray wands, frits, ionizing spray units, vaporizers, gas-liquid exchangers, freezer and chilling units, and the like. Venting can include spraying, atomizing, vaporizing, sputtering, freezing or freeze drying, fogging, frit bubbling, foaming, and the like. Any vessel suitable for containing and venting a pressurized fluid can be employed in the methods of the invention.

Once the composition including the fluid and antimicrobial agent leaves the applicator device with the associated pressure drop, the densified fluid quickly returns to the gaseous phase leaving an effective concentration of the antimicrobial agent on the contact surface. The evaporation of the fluid phase usually results in a substantial cooling effect. Typically, the cooling effect does not change the antimicrobial agent in any important way; however, such cooling can result in the creation of a solid phase of the antimicrobial agent on the contact surface until such time as ambient heat melts the material. The application pressure used in the application on the material to the surface can have, as a minimum, a pressure below the critical pressure if a near critical fluid is desired. However, with a supercritical fluid, the application pressure can be at or above the critical pressure of the supercritical fluid. The application pressure can be lower than the supercritical level. For example, if densified carbon dioxide is used, preferred spray pressures include about 300 psi to about 1200 psi. If supercritical carbon dioxide is used, preferred spray pressures include between about 1000 psi to about 3000 psi.

The spray temperature as used in the practice of the invention is typically a function of the concentration of the material in the working fluid and the need for near critical, critical or supercritical fluid properties. The maximum temperature is typically a temperature at which the components of the liquid mixture maintain the appropriate fluid properties and have no thermal degradation during storage or use. Because of the tendency of these working materials to cool upon application, the application of warmed material can often result in the creation of a liquid cleaner or sanitizer on the surface of the object without concerns with freezing resulting from heat of vaporization. The temperature of application typically is gauged by the critical temperature of the working fluid. However, the temperature can exceed the critical temperature of the working fluid as long as the working fluid and the active material remain stable at the useful temperatures. The temperature of the material may be adjusted by heating the container for the working fluid, the conduits, or the application device.

Spraying devices that can be used in the performance of the cleaning or sanitizing processes of the invention include virtually any spray applicator that can achieve the appropriate pressure drop across the spray exit in order to obtain a spray that can be easily distributed across the soiled or contaminated surface. If a spray is selected, the shape of the spray can be adjusted into an appropriate cone or fan shape. Application devices selected to improve the efficiency and rates of contact of the material onto the maximum surface area of the substrate. The sprays can be created using power assist mechanisms such as using additional spray media or inert dilution gas(es) to further facilitate the application of the materials.

In certain preferred methods for applying the compositions, the method delivers a mixture containing a higher proportion of antimicrobial agent than is present in the densified fluid composition from which it is produced. For example, venting the vessel containing the densified fluid and antimicrobial agent, can strip or preferentially deliver from the container antimicrobial agent, leaving behind greater quantities of other components of the composition. Although not limiting to the present invention, it is believed that before or during applying certain antimicrobial agents, such as peroxycarboxylic acids (e.g., peroxyacetic acid), are preferentially dissolved in or carried by the densified fluid. In particular, it has been observed that venting a densified fluid composition containing carbon dioxide, a peroxycarboxylic acid antimicrobial agent (e.g., peroxyacetic acid), and hydrogen peroxide preferentially releases peroxycarboxylic acid compared to hydrogen peroxide.

For or during application of the composition, the object, vessel, and vent can move in relation to one another. For example, applying can include transporting the object to the vessel and the vent, or transporting the vessel and/or the vent to the object. Applying can include moving the vent relative to the object during venting or between ventings at the object and/or moving the object relative to the vent during venting or between ventings at the object.

Densified fluid antimicrobial compositions can be applied in any of a variety of situations and to any of a variety of objects, such as ceramics, a food product, such as meat, poultry, or produce; a textile, such as a surgical garment; hospital decontamination equipment, surgical materials in a sterilizing unit, a nonwoven such as a filter; veterinary products such as mammalian skin treatments or in products for sanitizing or disinfecting animal enclosures, pens, watering stations, and veterinary treatment areas such as inspection tables and operation rooms.

Densified fluid antimicrobial compositions can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; air slicers and finished product packaging devices; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like.

Densified fluid antimicrobial compositions can be used on food and pharmaceutical packaging materials and equipment, and especially for cold or hot food/beverage, or pharmaceutical aseptic packaging. The compositions can also be used on or in ware wash machines, dishware, bottle washers, bottle chillers, warmers, third sink washers, cutting areas (e.g., water knives, slicers, cutters and saws) and egg washers. Particular foodstuffs that can be treated with compositions of the invention include eggs, meats, seeds, leaves, fruits and vegetables. Particular plant surfaces include both harvested and growing leaves, roots, seeds, skins or shells, stems, stalks, tubers, corms, fruit, and the like. Particular treatable surfaces include packaging such as cartons, bottles, films and resins; dishware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles.

Densified fluid antimicrobial compositions can also be used on or in other industrial equipment and in other industrial process streams such as heaters, cooling towers, boilers, retort waters, rinse waters, aseptic packaging wash waters, and the like. The compositions can be used to treat microbes and odors in recreational waters such as in pools, spas, recreational flumes and water slides, fountains, and the like.

Other hard surface cleaning applications for the densified fluid antimicrobial compositions of the invention include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like. CIP systems include a variety of known devices.

Applying Antimicrobial Agent and Densified Fluid to a Food, Beverage, or Pharmaceutical Product Contacting a food, beverage, or pharmaceutical product with a densified fluid antimicrobial composition can be accomplished by methods including modified atmosphere packaging (e.g., cut meat packages, aseptic packaging systems, anti-spoilage packaging, tableting machines), waterless chilling systems (e.g., meat chillers, refrigeration systems, carcass spray chambers), food-washing units, food transport equipment including sanitizing belt sprayers, fermentation tanks or other brewery units, and similar systems intended to reduce, selectively control, or eliminate the microbial loading on a food, beverage, or pharmaceutical product or package. The densified fluid antimicrobial composition can be applied to food, beverage, or pharmaceutical product by any of a variety of methods known for applying gaseous or densified liquid agents to food, beverage, or pharmaceutical product during processing, including air chilling, transport systems, and packaging (e.g. aseptic packaging, modified atmosphere packaging), particularly at steps where adding water or air to the food or beverage product is disadvantageous.

According to the present invention, modified atmosphere packaging, food washing or sanitizing, food chilling, or similar food processing step can be accomplished employing a densified fluid antimicrobial composition. Preferred densified fluid compositions for modified atmosphere packaging can include peroxycarboxylic acids, carboxylic acids, interhalides, polyhalides, chlorine dioxide, chlorine, and mixtures thereof.

Contacting meat with a densified fluid antimicrobial composition can take place in or employ meat chillers where meat carcasses are cooled before further processing to prevent spoilage, antimicrobial spray systems which reduce the microbial population on a carcass surface prior to chilling, and ready-to-eat meat slicing and packaging systems that take a processed meat product and slice or package a final meat product. One type of meat handling unit involves spray treatment of processed animal carcasses (e.g., beef, lamb) which might utilize a sanitizing spray after de-skinning and before chilling. Contacting with a densified fluid antimicrobial composition can be used as a substitute for the sanitizing spray.

Peroxycarboxylic Acid Antimicrobial Compositions
Compositions of Carboxylic Acids and Peroxycarboxylic Acids Among other constituents, the composition of the present invention includes a carboxylic acid. Generally, carboxylic acids have the formula R—COOH wherein the R can represent any number of different groups including aliphatic groups, alicyclic groups, aromatic groups, heterocyclic groups, all of which can be saturated or unsaturated as well as substituted or unsubstituted. Carboxylic acids can have one, two, three, or more carboxyl groups. The composition and methods of the invention can employ carboxylic acids containing as many as 18 carbon atoms. Examples of suitable carboxylic acids include formic, acetic, propionic, butanoic, pentanoic, hexanoic, heptanoic, octanoic, nonanoic, decanoic, undecanoic, dodecanoic, lactic, maleic, ascorbic, citric, hydroxyacetic, neopentanoic, neoheptanoic, neodecanoic, oxalic, malonic, succinic, glutaric, adipic, pimelic and suberic acid. Carboxylic acids which are generally useful are those having one or two carboxyl groups where the R group is a primary alkyl chain having a length of $C_2$ to $C_{12}$. The primary alkyl chain is that carbon chain of the molecule having the greatest length of carbon atoms and directly appending carboxyl functional groups. Octanoic acid can reduce surface tension to assist in wetting of hydrophobic surfaces like skin.

Peroxycarboxylic (or percarboxylic) acids generally have the formula $R(CO_3H)_n$, where R is an alkyl, arylalkyl, cycloalkyl, aromatic or heterocyclic group, and n is one, two, or three, and named by prefixing the parent acid with peroxy. While peroxycarboxylic acids are not as stable as carboxylic acids, their stability generally increases with increasing molecular weight. Thermal decomposition of these acids can generally proceed by free radical and non-radical paths, by photodecomposition or radical-induced decomposition, or by the action of metal ions or complexes. Percarboxylic acids can be made by the direct, acid catalyzed equilibrium action of hydrogen peroxide with the carboxylic acid, by autoxidation of aldehydes, or from acid chlorides, and hydrides, or carboxylic anhydrides with hydrogen or sodium peroxide.

Peroxycarboxylic acids useful in the compositions and methods of the present invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, peroxylactic, peroxymaleic, peroxyascorbic, peroxyhydroxyacetic, peroxyoxalic, peroxymalonic, peroxysuccinic, peroxyglutaric, peroxyadipic, peroxypimelic and peroxysuberic acid and mixtures thereof. Peroxy forms of carboxylic acids with more than one carboxylate moiety can have one or more of the carboxyl moieties present as peroxycarboxyl moieties. These peroxycarboxylic acids have been found to provide good antimicrobial action with good stability in aqueous mixtures. In a preferred embodiment, the composition of the invention utilizes a combination of several different peroxycarboxylic acids. Preferably, the composition includes one or more small $C_2$–$C_4$ peroxycarboxylic acids and one or more large $C_7$–$C_9$ peroxycarboxylic acids. Especially preferred is an embodiment in which the small peroxycarboxylic acid is peroxyacetic acid and the large acid is peroxyoctanoic acid.

Suitable peroxycarboxylic acids include ester peroxycarboxylic acids having the formula:

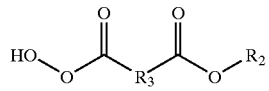

In this formula, $R_2$ and $R_3$ can independently be any of a wide variety of organic groups (e.g. alkyl, linear or cyclic, aromatic or saturated) or substituted organic groups (e.g., with one or more heteroatoms or organic groups). Ester peroxycarboxylic acid can be made using methods typically employed for producing peroxycarboxylic acid, such as incubating the corresponding monoester or diester dicarboxylate with hydrogen peroxide.

Preferred ester peroxycarboxylic acids include alkyl ester peroxycarboxylic acids having the formula:

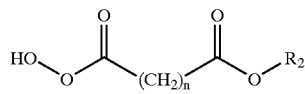

where $R_2$ represents an alkyl group having from 1 to 8 carbons and n is 0 to 6, preferably 1 to 5. The alkyl group can be either straight chain or branched. Preferably, $R_2$ is a methyl, ethyl, propyl (n- or iso-), butyl (n-, iso-, or tert-), n-amyl, n-hexyl, or 2-ethylhexyl group. Preferably, n is 2, 3, 4, or 5. In an embodiment, the composition of the present invention includes a mixture of alkyl ester peroxycarboxylic acids in which n is 2, 3, and 4. Such a mixture includes monoesters of peroxyadipic, peroxyglutaric, and peroxysuccinic acids. In an embodiment, a majority of the ester peroxycarboxylic acid in the composition has x equal to 3. In an embodiment, $R_2$ is a $C_1$–$C_8$ alkyl. In an embodiment, n is 1, 2, 3, or 4. Preferably, $R_2$ is a $C_1$ alkyl, $C_2$ alkyl, $C_3$ alkyl, or $C_4$ alkyl, and n is 2, 3 or 4, or a combination thereof. In an embodiment, $R_2$ is a $C_5$–$C_8$ alkyl and n is 5 or 6.

Alkyl ester peroxycarboxylic acids useful in this invention include monomethyl monoperoxyoxalic acid, monomethyl monoperoxymalonic acid, monomethyl monoperoxysuccinic acid, monomethyl monoperoxyglutaric acid, monomethyl monoperoxyadipic acid, monomethyl monoperoxysebacic acid; monoethyl monoperoxyoxalic acid, monoethyl monoperoxymalonic acid, monoethyl monoperoxysuccinic acid, monoethyl monoperoxyglutaric acid, monoethyl monoperoxyadipic acid, monoethyl monoperoxysebacic acid; monopropyl monoperoxyoxalic acid, monopropyl monoperoxymalonic acid, monopropyl monoperoxysuccinic acid, monopropyl monoperoxyglutaric acid, monopropyl monoperoxyadipic acid, monopropyl monoperoxysebacic acid, in which propyl can be n- or iso-propyl; monobutyl monoperoxyoxalic acid, monobutyl monoperoxymalonic acid, monobutyl monoperoxysuccinic acid, monobutyl monoperoxyglutaric acid, monobutyl monoperoxyadipic acid, monobutyl monoperoxysebacic acid, in which butyl can be n-, iso-, or t-butyl; monoamyl monoperoxyoxalic acid, monoamyl monoperoxymalonic acid, monoamyl monoperoxysuccinic acid, monoamyl monoperoxyglutaric acid, monoamyl monoperoxyadipic acid, monoamyl monoperoxysebacic acid, in which amyl is n-; monohexyl monoperoxysebacic acid, in which hexyl is n-; mono-2-ethylhexyl monoperoxysebacic acid.

Typically, the compositions and methods of the present invention include peroxyacetic acid. Peroxyacetic (or peracetic) acid is a peroxycarboxylic acid having the formula: $CH_3COOOH$. Generally, peroxyacetic acid is a liquid having an acrid odor at higher concentrations and is freely soluble in water, alcohol, ether, and sulfuric acid. Peroxyacetic acid can be prepared through any number of methods known to those of skill in the art including preparation from acetaldehyde and oxygen in the presence of cobalt acetate. A solution of peroxyacetic acid can be obtained by combining acetic acid with hydrogen peroxide. A 50% solution of peroxyacetic acid can be obtained by combining acetic anhydride, hydrogen peroxide and sulfuric acid. Other methods of formulation of peroxyacetic acid include those disclosed in U.S. Pat. No. 2,833,813, which is incorporated herein by reference.

Typically, the compositions and methods of the present invention include peroxyoctanoic acid, peroxynonanoic acid, or peroxyheptanoic acid, preferably peroxyoctanoic acid. Peroxyoctanoic (or peroctanoic) acid is a peroxycarboxylic acid having the formula, for example, of n-peroxyoctanoic acid: $CH_3(CH_2)_6COOOH$. Peroxyoctanoic acid can be an acid with a straight chain alkyl moiety, an acid with a branched alkyl moiety, or a mixture thereof. Peroxyoctanoic acid can be prepared through any number of methods known to those of skill in the art. A solution of peroxyoctanoic acid can be obtained by combining octanoic acid and hydrogen peroxide.

A preferred antimicrobial composition of the present invention includes acetic acid, octanoic acid, peroxyacetic acid, and peroxyoctanoic acid. Such a composition can also include a chelating agent. A preferred composition preferably includes a combination of peroxyacetic acid and peroxyoctanoic acid effective for killing one or more of the food-borne pathogenic bacteria associated with a food product, such as *Salmonella typhimurium, Salmonella javiana, Campylobacter jejuni, Listeria monocytogenes,* and *Escherichia coli* O157:H7, yeast, mold and the like. The compositions and methods of the present invention have activity against a wide variety of microorganisms such as Gram positive (for example, *Listeria monocytogenes*) and Gram negative (for example, *Escherichia coli*) bacteria, yeast, molds, bacterial spores, viruses, etc. The compositions and methods of the present invention, as described above, have activity against a wide variety of human pathogens. The compositions and methods can kill a wide variety of microbes on the surface of a food product or in water used for washing or processing of food product.

The preferred compositions include concentrate compositions and use compositions. Typically, an antimicrobial concentrate composition can be diluted, for example with water, to form an antimicrobial use composition. In a preferred embodiment, the concentrate composition is diluted into water employed for washing or processing food product.

The advantageous stability of mixed peroxycarboxylic acid compositions in such methods, which include the presence of food product debris or residue, makes these compositions competitive with cheaper, less stable, and potentially toxic chlorinated compounds. Preferred methods of the present invention include agitation or sonication of the use composition, particularly as a concentrate is added to water to make the use composition. Preferred methods include water systems that have some agitation, spraying, or other mixing of the solution.

A variety of peroxycarboxylic acid antimicrobial compositions are known to those of skill in the art. Densified fluid compositions that apply effective antimicrobial amounts of the peroxycarboxylic acids and mixtures described in these patent documents can be employed in the methods of the present invention. Similarly, extracting such compositions with a densified fluid can provide a useful densified fluid antimicrobial composition. Suitable compositions are disclosed in U.S. Pat. No. 6,010,729, issued Jan. 4, 2000 to Gutzmann et al.; U.S. Pat. No. 5,718,910, issued Feb. 17, 1998 to Oakes et al.; U.S. Pat. No. 5,674,538, issued May 24, 1994 to Lokkesmoe et al.; U.S. Pat. No. 5,349,434, issued Feb. 6, 1996 to Oakes et al.; U.S. Pat. No. 5,437,868, issued Aug. 1, 1995 to Oakes et al.; U.S. Pat. No. 5,409,713, issued Apr. 25, 1995 to Lokkesmoe et al.; U.S. Pat. No. 5,314,687, issued May 24, 1994 to Oakes et al.; and U.S. Pat. No. 5,200,189, issued Apr. 6, 1993 to Oakes et al.; which are incorporated herein by reference for disclosure of these compositions and methods for applying them.

A mixture of peroxyacetic acid with peroxyoctanoic acid is described in U.S. patent application Ser. No. 09/738,306 entitled METHOD AND COMPOSITION FOR WASHING POULTRY DURING PROCESSING, which was filed Dec. 15, 2000, now issued as U.S. Pat. No. 6,514,556. This patent application is incorporated herein by reference for disclosure of these compositions. These compositions include an antimicrobial concentrate composition of about 40 to about 70 weight-%, preferably about 45 to about 65 weight-%, preferably about 50 to about 60 weight-% acetic acid; about 2 to about 20 weight-%, preferably about 2 to about 8 weight-% octanoic acid; and about 5 to about 15 weight-% hydrogen peroxide. Preferably, such an antimicrobial concentrate composition includes about 55 weight-% acetic acid, about 11 weight-% hydrogen peroxide, and about 4 weight-% octanoic acid. A preferred antimicrobial concentrate composition of the present invention includes about 30 to about 60 weight-%, preferably about 35 to about 60 weight-%, preferably about 35 to about 50 weight-%, preferably about 40 to about 50 weight-% acetic acid; about 1 to about 15 weight-%, preferably about 1 to about 7 weight-% octanoic acid; about 2 to about 12 weight-%, preferably about 2 to about 8 weight-% hydrogen peroxide; about 6 to about 16 weight-%, preferably about 8 to about 16 weight-% peroxyacetic acid; and about 0.1 to about 5 weight-%, preferably about 0.1 to about 2 weight-% peroxyoctanoic acid. Preferably, such an antimicrobial concentrate composition includes about 40 weight-% acetic acid, about 3 weight-% octanoic acid, about 6 weight-% hydrogen peroxide, about 10 weight-% peroxyacetic acid, and about 0.8 weight-% peroxyoctanoic acid. Preferably, such an antimicrobial concentrate composition includes about 41 weight-% acetic acid, about 3.2 weight-% octanoic acid, about 6.2 weight-% hydrogen peroxide, about 12 weight-% peroxyacetic acid) and about 0.80 weight-% perexyoctanoic acid.

Another mixture of peroxyacetic acid with peroxyoctanoic acid is described in U.S. patent application Ser. No. 09/614,631 filed Jul. 12, 2000 and entitled METHOD AND COMPOSITION FOR INHIBITION OF MICROBIAL GROWTH IN AQUEOUS FOOD TRANSPORT AND PROCESS STREAMS. This patent application is incorporated herein by reference for disclosure of these compositions. A preferred antimicrobial concentrate composition includes about 50 to about 60 weight-% acetic acid, about 10 to about 20 weight-% octanoic acid, about 5 to about 15 weight-% hydrogen peroxide, and about 0.3 to about 1 weight-% chelating agent. Preferably, such an antimicrobial concentrate composition includes about 54 weight-% acetic acid, about 10 weight-% hydrogen peroxide, about 0.6 weight-% chelating agent, and about 14 weight-% octanoic acid. A preferred antimicrobial concentrate composition of the present invention includes about 35 to about 45 weight-% acetic acid, about 5 to about 15 weight-% octanoic acid, about 3 to about 8 weight-% hydrogen peroxide, about 8 to about 16 weight-% peroxyacetic acid, about 1 to about 5 weight-% peroxyoctanoic acid, and about 0.1 to about 2 weight-% chelating agent. Preferably, such an antimicrobial concentrate composition includes about 40 weight-% acetic acid, about 10 weight-% octanoic acid, about 5 weight-% hydrogen peroxide, about 12 weight-% peroxyacetic acid, about 3 weight-% peroxyoctanoic acid, and about 0.6 weight-% chelating agent.

In each of the compositions described above, the chelating agent is an optional, but preferred, ingredient. Typically the balance of each of the compositions described above is made up primarily or exclusively of a solvent, such as water, e.g. tap or other potable water.

The compositions of the present invention preferably include only ingredients that can be employed in food products or in food product washing, handling, or processing, for example, according to government (e.g. FDA or USDA) rules and regulations. Preferably, the composition is free of any peroxycarboxylic acid or carboxylic acid with 10, 12, or more carbon atoms. Such 10, 12, or more carbon acids can impart undesirable residues (e.g. bad tasting and/or malodorous) to food product.

Hydrogen Peroxide

The antimicrobial compositions of the invention typically also include a hydrogen peroxide constituent. Hydrogen peroxide in combination with the percarboxylic acid provides certain antimicrobial action against microorganisms. Additionally, hydrogen peroxide can provide an effervescent action which can irrigate any surface to which it is applied. Hydrogen peroxide works with a mechanical flushing action once applied which further cleans the surface. An additional advantage of hydrogen peroxide is the food compatibility of this composition upon use and decomposition. For example, combinations of peroxyacetic acid, peroxyoctanoic acid, and hydrogen peroxide result in acetic acid, octanoic acid, water, and oxygen upon decomposition, all of which are food product compatible.

Many oxidizing agents can be used for generating peroxycarboxylic acids. Suitable oxidizing agents, in addition to hydrogen peroxide, include perborate, percarbonate, and persulfate. Hydrogen peroxide is generally preferred for several reasons. After application of the $H_2O_2$/peroxycarboxylic acid germicidal agent, the residue left merely includes water and an acidic constituent. Deposition of these products on the surface of a food product processing apparatus, such as a bath or spray apparatus, will not adversely effect the apparatus, the handling or processing, or the food product washed therein.

Hydrogen peroxide ($H_2O_2$), has a molecular weight of 34.014 and it is a weakly acidic, clear, colorless liquid. The four atoms are covalently bonded in a H—O—O—H structure. Generally, hydrogen peroxide has a melting point of −0.41° C., a boiling point of 150.2° C., a density at 25° C. of 1.4425 grams per $cm^3$, and a viscosity of 1.245 centipoise at 20° C.

Carrier

The composition of or employed in the method of the invention also includes a carrier. The carrier provides a medium which dissolves, suspends, or carries the other components of the composition. For example, the carrier can provide a medium for solubilization and production of peroxycarboxylic acid and for forming an equilibrium mixture. The carrier also functions to deliver and wet the antimicrobial composition of the invention to the food product. To this end, the carrier may contain any component or components that can facilitate these functions.

Generally, the carrier includes primarily water which is an excellent solubilizer and medium for reaction and equilibrium. The carrier can include or be primarily an organic solvent, such as simple alkyl alcohols, e.g., ethanol, isopropanol, n-propanol, and the like. Polyols are also useful carriers, including propylene glycol, polyethyleneglycol, glycerol, sorbitol, and the like. Any of these compounds may be used singly or in combination with other organic or inorganic constituents or, in combination with water or in mixtures thereof.

Generally, the carrier makes up a large portion of the composition and may be the balance of the composition apart from the active antimicrobial components, adjuvants, and the like. Here again, the carrier concentration and type will depend upon the nature of the composition as a whole, the environmental storage, and method of application including concentration of the antimicrobial agent, among other factors. Notably the carrier should be chosen and used at a concentration which does not inhibit the antimicrobial efficacy of the active agent in the composition.

Adjuvants

The antimicrobial composition of or employed in the method of the invention can also include any number of adjuvants. Specifically, the composition can include stabilizing agents, wetting agents, hydrotropes, thickeners, a surfactant, foaming agents, acidifiers, as well as pigments or dyes among any number of constituents which can be added to the composition. Such adjuvants can be preformulated with the antimicrobial composition or added to the system simultaneously, or even after, the addition of the antimicrobial composition. The composition can also contain any number of other constituents as necessitated by the application, which are known to those of skill in the art and which can facilitate the activity of the present invention.

Stabilizing Agents

Stabilizing agents can be added to the composition, for example, to stabilize the peracid and hydrogen peroxide and prevent the premature oxidation of this constituent within the composition.

Chelating agents or sequestrants generally useful as stabilizing agents in the present compositions include alkyl diamine polyacetic acid-type chelating agents such as EDTA (ethylene diamine tetraacetate tetrasodium salt), acrylic and polyacrylic acid-type stabilizing agents, phosphonic acid, and phosphonate-type chelating agents among others. Preferable sequestrants include phosphonic acids and phosphonate salts including 1-hydroxy ethylidene-1,1-diphosphonic acid ($CH_3C(PO_3H_2)_2OH$) (HEDP), amino[tri(methylene phosphonic acid)] ($[CH_2PO_3H_2]_2$(ethylene diamine[tetra methylene-phosphonic acid)], 2-phosphene butane-1,2,4-tricarboxylic acid, as well as the alkyl metal salts, ammonium salts, or alkyloyl amine salts, such as mono, di, or tetra-ethanolamine salts. The stabilizing agent is used in a concentration ranging from about 0 weight percent to about 20 weight percent of the composition, preferably from about 0.1 weight percent to about 10 weight percent of the composition, and most preferably from about 0.2 weight percent to 5 weight percent of the composition.

Amino phosphates and phosphonates are also suitable for use as chelating agents in the compositions and include ethylene diamine (tetramethylene phosphonates), nitrilotrismethylene phosphates, diethylenetriamine (pentamethylene phosphonates). These amino phosphonates commonly contain alkyl or alkaline groups with less than 8 carbon atoms. The phosphonic acid may also include a low molecular weight phosphonopolycarboxylic acid such as one having about 2–4 carboxylic acid moieties and about 1–3 phosphonic acid groups. Such acids include 1-phosphono-1-methylsuccinic acid, phosphonosuccinic acid and 2-phosphonobutane-1,2,4-tricarboxylic acid.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino(tri(methylenephosphonic acid)), ($N[CH_2PO_3H_2]_3$), available from Monsanto as DEQUEST® 2000; ethylenediamine[tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The above-mentioned phosphonic acids can also be used in the form of water soluble acid salts, particularly the alkali metal salts, such as sodium or potassium; the ammonium salts or the alkylol amine salts where the alkylol has 2 to 3 carbon atoms, such as mono-, di-, or triethanolamine salts. If desired, mixtures of the individual phosphonic acids or their acid salts can also be used.

The concentration of chelating agent useful in the present invention generally ranges from about 0.01 to about 10 wt-%, preferably from about 0.1 to about 5 wt-%, most preferably from about 0.5 to about 2 wt-%.

Wetting or Defoaming Agents

Also useful in the composition are wetting and defoaming agents. Wetting agents function to increase the surface contact or penetration activity of the antimicrobial composition. Wetting agents which can be used in the composition include any of those constituents known within the art to raise the surface activity of the composition.

Along these lines, surfactants, and especially nonionic surfactants, can also be useful in the present invention. Nonionic surfactants which can be useful in the present invention are those which include ethylene oxide moieties, propylene oxide moieties, as well a mixtures thereof, and ethylene oxide-propylene oxide moieties in either heteric or block formation. Additionally useful in the present invention are nonionic surfactants which include an alkyl ethylene oxide compounds, alkyl propylene oxide compounds, as well as mixtures thereof, and alkyl ethylene oxide-propylene oxide compounds where the ethylene oxide propylene oxide moiety is either in heteric or block formation. Further useful in the present invention are nonionic surfactants having any mixture or combination of ethylene oxide-propylene oxide moieties linked to a alkyl chain where the ethylene oxide and propylene oxide moieties can be in any randomized or ordered pattern and of any specific length. Nonionic surfactants useful in the present invention can also include randomized sections of block and heteric ethylene oxide propylene oxide, or ethylene oxide-propylene oxide, such as ethylene diamine ethylene oxides, ethylene diamine propylene oxides, mixtures thereof, and ethylene diamine EO-PO compounds, including those sold under the tradename Tetronic.

Generally, the concentration of nonionic surfactant used in a composition of the present invention can range from about 0 wt-% to about 5 wt-% of the composition, preferably from about 0 wt-% to about 2 wt-% of the concentrate composition, and most preferably from about 0 wt-% to about 1 wt-% of the composition.

The composition can also contain additional ingredients as necessary to assist in defoaming. Generally, defoamers which can be used in accordance with the invention include silica and silicones; aliphatic acids or esters; alcohols;

sulfates or sulfonates; amines or amides; halogenated compounds such as fluorochlorohydrocarbons; vegetable oils, waxes, mineral oils as well as their sulfated derivatives; fatty acid soaps such as alkali, alkaline earth metal soaps; and phosphates and phosphate esters such as alkyl and alkaline diphosphates, and tributyl phosphates among others; and mixtures thereof.

Especially preferable, are those antifoaming agents or defoamers which are of food grade quality given the application of the method of the invention. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others. These defoamers can be present at a concentration range from about 0.01 wt-% to 5 wt-%, preferably from about 0.01 wt-% to 2 wt-%, and most preferably from about 0.01 wt-% to about 1 wt-%.

Hydrotrope

The food product wash composition of the invention or employed in the method of the invention can also include a hydrotrope coupler or solubilizer. Such materials can be used to ensure that the composition remains phase stable and in a single highly active aqueous form. Such hydrotrope solubilizers or couplers can be used at compositions which maintain phase stability but do not result in unwanted compositional interaction.

Representative classes of hydrotrope solubilizers or coupling agents include an anionic surfactant such as an alkyl sulfate, an alkyl or alkane sulfonate, a linear alkyl benzene or naphthalene sulfonate, a secondary alkane sulfonate, alkyl ether sulfate or sulfonate, an alkyl phosphate or phosphonate, dialkyl sulfosuccinic acid ester, sugar esters (e.g., sorbitan esters) and a $C_{8-10}$ alkyl glucoside.

Preferred coupling agents for use in the present compositions and methods include n-octane sulfonate and aromatic sulfonates such as an alkyl aryl sulfonate (e.g., sodium xylene sulfonate or naphthalene sulfonate). Many hydrotrope solubilizers independently exhibit some degree of antimicrobial activity at low pH. Such action adds to the efficacy of the invention but is not a primary criterion used in selecting an appropriate solubilizing agent. Since the presence of the peroxycarboxylic acid material in the protonated neutral state provides beneficial biocidal or antimicrobial activity, the coupling agent should be selected not for its independent antimicrobial activity but for its ability to provide effective single phase composition stability in the presence of substantially insoluble peroxycarboxylic acid materials and the more soluble compositions of the invention. Generally, any number of surfactants may be used consistent with the purpose of this constituent.

Anionic surfactants useful with the invention include alkyl carboxylates, linear alkylbenzene sulfonates, paraffin sulfonates and secondary n-alkane sulfonates, sulfosuccinate esters and sulfated linear alcohols.

Zwitterionic or amphoteric surfactants useful with the invention include β-N-alkylaminopropionic acids, n-alkyl-β-iminodipropionic acids, imidazoline carboxylates, n-alkyl-Iletaines, amine oxides, sulfobetaines and sultaines.

Nonionic surfactants useful in the context of this invention are generally polyether (also known as polyalkylene oxide, polyoxyalkylene or polyalkylene glycol) compounds. More particularly, the polyether compounds are generally polyoxypropylene or polyoxyethylene glycol compounds. Typically, the surfactants useful in the context of this invention are synthetic organic polyoxypropylene (PO)-polyoxyethylene (EO) block copolymers. These surfactants have a diblock polymer including an EO block and a PO block, a center block of polyoxypropylene units (PO), and having blocks of polyoxyethylene grated onto the polyoxypropylene unit or a center block of EO with attached PO blocks. Further, this surfactant can have further blocks of either polyoxyethylene or polyoxypropylene in the molecule. The average molecular weight of useful surfactants ranges from about 1000 to about 40,000 and the weight percent content of ethylene oxide ranges from about 10–80% by weight.

Also useful in the context of this invention are surfactants including alcohol alkoxylates having EO, PO and BO blocks. Straight chain primary aliphatic alcohol alkoxylates can be particularly useful as sheeting agents. Such alkoxylates are also available from several sources including BASF Wyandotte where they are known as "Plurafac" surfactants. A particular group of alcohol alkoxylates found to be useful are those having the general formula $R\text{-}(EO)_m\text{-}(PO)_n$ wherein m is an integer of about 2–10 and n is an integer from about 2–20. R can be any suitable radical such as a straight chain alkyl group having from about 6–20 carbon atoms.

Other useful nonionic surfactants include capped aliphatic alcohol alkoxylates. These end caps include but are not limited to methyl, ethyl, propyl, butyl, benzyl and chlorine. Useful alcohol alkoxylated include ethylene diamine ethylene oxides, ethylene diamine propylene oxides, mixtures thereof, and ethylene diamine EO-PO compounds, including those sold under the tradename Tetronic. Preferably, such surfactants have a molecular weight of about 400 to 10,000. Capping improves the compatibility between the nonionic and the oxidizers hydrogen peroxide and peroxycarboxylic acid, when formulated into a single composition. Other useful nonionic surfactants are alkylpolyglycosides.

Another useful nonionic surfactant is a fatty acid alkoxylate wherein the surfactant includes a fatty acid moiety with an ester group including a block of EO, a block of PO or a mixed block or heteric group. The molecular weights of such surfactants range from about 400 to about 10,000, a preferred surfactant has an EO content of about 30 to 50 wt-% and wherein the fatty acid moiety contains from about 8 to about 18 carbon atoms.

Similarly, alkyl phenol alkoxylates have also been found useful in the invention. Such surfactants can be made from an alkyl phenol moiety having an alkyl group with 4 to about 18 carbon atoms, can contain an ethylene oxide block, a propylene oxide block or a mixed ethylene oxide, propylene oxide block or heteric polymer moiety. Preferably such surfactants have a molecular weight of about 400 to about 10,000 and have from about 5 to about 20 units of ethylene oxide, propylene oxide or mixtures thereof.

The concentration of hydrotrope useful in the present invention generally ranges from about 0.1 to about 20 wt-%, preferably from about 0.5 to about 10 wt-%, most preferably from about 1 to about 4 wt-%.

Thickening or Gelling Agents

Thickeners useful in the present invention include those which do not leave contaminating residue on the surface of food product or food product processing apparatus. That is, preferred thickeners or gelling agents do not include components incompatible with food or other sensitive products in contact areas.

Generally, thickeners which may be used in the present invention include natural gums such as xanthan gum, guar gum, or other gums from plant mucilage; polysaccharide based thickeners, such as alginates, starches, and cellulosic polymers (e.g., carboxymethyl cellulose); polyacrylates thickeners; and hydrocolloid thickeners, such as pectin. Generally, the concentration of thickener employed in the present compositions or methods will be dictated by the desired viscosity within the final composition. However, as a general guideline, the viscosity of thickener within the present composition ranges from about 0.1 wt-% to about 1.5 wt-%, preferably from about 0.1 wt-% to about 1.0 wt-%, and most preferably from about 0.1 wt-% to about 0.5 wt-%.

Additional Antimicrobial Agents

The present methods can employ antimicrobial compositions including any of a variety of antimicrobial agents. Such antimicrobial agents include quaternary ammonium antimicrobial agents, acid sanitizers, and other food surface compatible antimicrobial agents.

Quaternary Ammonium Antimicrobial Agents

Quaternary ammonium antimicrobial agents are useful in the present invention, due to their commercial availability, easy incorporation into formulas and high sanitizing efficacy. These sanitizing agents are also preferred because of their compatibility to high water temperatures to the presence of high organic loads, stability and broad spectrum antimicrobial efficacy in variable high and low pH wash systems, inherent chemical deodorizing, and their non-staining, non-bleaching, non-corrosive nature.

Suitable agents which may be incorporated are quaternary ammonium salts of the formula:

$$[R_1R_2R_3R_4N]+Y^-$$

in which at least one, but not more than two, of $R_1$, $R_2$, $R_3$, and $R_4$ is an organic radical containing a group selected from a $C_{16}$–$C_{22}$ aliphatic radical, or an alkyl phenyl or alkyl benzyl radical having 10–16 atoms in the alkyl chain, the remaining group or groups being selected from hydrocarbyl groups containing from 1 to about 4 carbon atoms, or $C_2$–$C_4$ hydroxy alkyl groups and cyclic structures in which the nitrogen atom forms part of the ring, and Y is an anion such as halide, methylsulphate, or ethylsulphate.

In the context of the above definition, the hydrophobic moiety (i.e. the $C_{16}$–$C_{22}$ aliphatic, $C_{10}$–$C_{16}$ alkyl phenyl or alkyl benzyl radical) in the organic radical may be directly attached to the quaternary nitrogen atom or may be indirectly attached thereto through an amide, esters, alkoxy, ether, or like grouping.

Illustrative quaternary ammonium salts include distearyl dimethyl ammonium chloride, stearyl dimethyl benzyl ammonium chloride, coconut alkyl dimethyl benzyl ammonium chloride, dicoconut alkyl dimethyl ammonium bromide, cetyl pyridinium iodide, and cetyl pyridinium iodide, and cetyl trimethyl ammonium bromide, and the like.

Carboxylic Acid Sanitizers

Suitable carboxylic acids for the antimicrobial composition include a food surface compatible aliphatic or aromatic fatty acid, either saturated or unsaturated, preferably, saturated, and having from about 2 to about 20 carbon atoms and, preferably, from about 2 to about 12 carbon atoms, most preferably 3 to 8, as well as mixtures thereof. The carboxylic acid can be linear, branched or cyclic and can contain substituent atoms such as hydroxyl groups or ether linkages as long as the substituents do not affect antimicrobial activity. Preferably, the carboxylic acid employed is food surface compatible, linear, saturated and unsubstituted. Representative carboxylic acids contemplated for use herein include formic, acetic, butyric, succinic, maleic, glycolic, lactic, caproic acid, caprylic acid, capric acid, lauric acid, and octanoic acid as well as mixtures thereof.

Halogen Containing Sanitizers

The present compositions can include iodo-compounds or active halogen compounds such as iodine or halogen complexes like alkaline BrCl, or interhalides like IBr, ICl, $ICl_2$, $ICl_4$, or polyhalides like $I_x$ x=3–9, or acid/metal hypochlorites like HOCl, NaOCl, $CaOCl_2$, or acid/metal hypobromites like HOBr, NaOBr, or chloro- and/or bromohydantoins, or chlorine dioxide and sodium chlorite. Preferred halides include iodide, bromide, and chloride, and mixtures thereof.

Other Antimicrobial Agents

Chemical compositions known to impart sanitizing efficacy include aldehydes, carboxylic acids, peracids and peroxygen compounds, iodine and iodine complexes, interhalogens, phenolics, surface-active agents including acid-anionic, amphoteric and cationic surfactants, nitrogen compounds and polymers including alkylamines, and inorganic and organic halogen releasing agent such as chlorine, chlorine dioxide and mixtures thereof. Such antimicrobial agents can be employed in the compositions and methods of the present invention.

Other Ingredients

Chelating agents can be added with any of these additional antimicrobial agents to the composition to enhance biological activity and cleaning performance. For example, one-hydroxy ethylidene-1, one-di-phosphonic acid commercially available from the Monsanto Company under the trade designation "Dequest" has been found to assist in the disruption of cell structure of the polysaccharide-divalent metal ion complex thought to exist in gram negative microorganisms. Citric acid is also found to interrupt such gram negative microorganism complexes. Other materials which are sufficiently stable at the low pH contemplated by the present composition may be added to the composition to impart desirable qualities depending upon the intended ultimate use.

Alkyl phosphate esters possess some antimicrobial activity in their own right under the conditions of the present invention. This antimicrobial activity also tends to add to the overall antimicrobial activity of the present compositions even though the phosphate esters may be added for other reasons.

Other materials can be added to the invention to change its color or odor, to adjust its viscosity, to enhance its thermal (i.e., freeze-thaw) stability or to provide other qualities which tend to make it more marketable. For example, isopropanol, ethanol or generally-recognized-as-safe (GRAS) flavoring agents of the ethyl fatty acid esters, in small amounts (e.g., approximately 0.1 to 0.2%) can be added to the composition to reduce viscosity or to reduce fatty acid odor.

The present invention may be better understood with reference to the following examples. These examples are intended to be representative of specific embodiments of the invention, and are not intended as limiting the scope of the invention.

EXAMPLES

Example 1

In-Situ Peroxycarboxylic Acid Production and Non-Aqueous Delivery of a Peroxycarboxylic Acid Spray A system including a densified fluid was employed for generating and delivering an antimicrobial agent.

Materials and Methods

The experiments were done with an Applied Separations Speed Supercritical Fluid Extraction system. A composition including 10.52 g acetic acid, 12.20 g $H_2O_2$, 0.36 g Dequest® and 0.91 g deionized (DI) water was injected into the stainless steel reaction chamber. The $CO_2$ pressure of the system was brought to 350 bar, by adding liquid carbon dioxide to fill the 100 ml reaction vessel. Then, the system was heated to a temperature of 80° C. The system was processed for one hour. Processing included cooling the vessel, venting off the $CO_2$, and measuring the gas-phase concentration of peracid, using a peracid test strip, in the vented $CO_2$.

Results

The vent gas was tested for the presence of peroxyacetic acid using a peracid test strip from Merck. Within a second of exposure, the peracid test strip registered levels in great excess of 50 ppm.

Conclusion

A densified fluid system successfully generated and delivered an antimicrobial agent. In particular, peroxyacetic acid was produced in the supercritical $CO_2$ environment and a significant amount of it was delivered from the system via the vented $CO_2$ gas. The quantity of antimicrobial agent produced and delivered by the densified fluid system was determined and found to be substantial.

Example 2

Peroxyacetic Acid Concentrations Collected from Vented $CO_2$

A densified fluid system was employed for generating and delivering a peracid antimicrobial agent.

Materials and Methods

An in-situ peroxyacetic acid (POAA) preparation was processed in the supercritical fluid extraction system to produce peroxyacetic acid as described in Example 1 with the differences described below. The in-situ peracid composition (8 ml total volume) was processed in the supercritical fluid extraction (SFE) system at a pressure of 200 bar and temperature of 80° C. for one hour. The reaction chamber was periodically agitated manually during the processing. After processing, the gas was slowly vented and bubbled through a small (2.5 ml) glass vial containing 1 ml of DI water in order to collect the peroxyacetic acid. The peroxyacetic acid was collected from the vent gas in this manner for time periods of 30 seconds, two minutes and five minutes. Two sets of collections were done, the first at a very low bubble rate and the second at a somewhat higher rate. The $CO_2$ vent gas flow rate had to be kept quite low in order that the bubbling would not force water into, from the extraction vessel, or out of the small collection vial. The water was then titrated to determine the concentration of peracid that had been collected.

Results

Table 1 shows the peracid concentrations found in the water through which the vent gas was bubbled. With a slow bubble rate (experiment 1), a peracid concentration of 500 ppm was found after 30 seconds of collection, 3000 ppm was found after two minutes of collection, and 6500 ppm was found after five minutes. The bubble rate was increased for experiment 2, and a peracid level of 2500 ppm was found after 30 seconds, 10,000 ppm was found after two minutes, and 15,000 ppm was found after five minutes.

TABLE 1

Peracid Levels Collected from Vented $CO_2$ Gas

| | | Peracid Level[1] Collection Time | | |
|---|---|---|---|---|
| | $CO_2$ Vent Characteristics[2] | 30 Seconds | 2 Minutes | 5 Minutes |
| 1 | Slow Bubble Rate | 500 ppm | 3000 ppm | 6500 ppm |
| 2 | Moderate Bubble Rate | 2500 ppm | 10,000 ppm | 15,000 ppm |

[1]Measured by Matrix/Vortex titration.
[2]$CO_2$ gas bubbled through 1 ml DI water in small collection vial.

Conclusion

Substantial amounts of antimicrobial agent were recovered by venting a mixture of densified fluid and antimicrobial agent. In particular, substantial concentrations of peroxy acid were recovered from venting of a densified carbon dioxide composition.

Example 3

Preferential Extraction of Peroxyacetic Acid over $H_2O_2$ from Reaction Chamber The concentrations of peroxy acid and hydrogen peroxide vented from the chamber of densified fluid were measured to determine whether peroxy acid was vented preferentially.

Materials and Methods

An in-situ peracid composition preparation was processed in the supercritical fluid extraction system to produce peroxyacetic acid and processed as described above in Examples 1 and 2, with the differences described below. After processing, the $CO_2$ gas was slowly vented from the system through a small vial cooled in a dry ice bath to collect the peroxyacetic acid and $H_2O_2$ from the vented gas. The collection was done until the reaction chamber was completely vented. The collected, and remaining, solutions were then titrated to determine the concentrations of peroxyacetic acid and $H_2O_2$ that had been collected or remained, respectively.

Results

Table 2 shows the peracid and $H_2O_2$ concentrations found in the solution collected from the vent gas, as well as those of the solution from the reaction chamber. The weight ratio of peracid to $H_2O_2$ was found to be much larger (>20 times increased) in the vent vial solution than in the reaction chamber solution.

TABLE 2

Peracid and $H_2O_2$ Levels in Vented $CO_2$ Gas

| | | Peracid | $H_2O_2$ | Peracid/$H_2O_2$ (weight ratio) |
|---|---|---|---|---|
| 1 | Reaction Chamber[1] | 5% | 21% | 0.24 |
| 2 | Vent Vial[2] | 5% | 1% | 5.0 (>20x increase) |

[1]Processed in Reaction Chamber, at 200 bar $CO_2$ pressure, 80° C.
[2]Collected from $CO_2$ vent gas by freezing in vial Conclusion Relatively little $H_2O_2$ was extracted in the vent gas compared to the amount of peracid extracted.

Example 4

Peroxyacetic Acid Antimicrobial Efficacy in Solution Test

The antimicrobial agent vented from a composition of a densified fluid was tested and found to be active.

Materials and Methods

The efficacy of peroxyacetic acid antimicrobial delivered via $CO_2$ gas was tested through an aqueous suspension test against *Escherichia coli* and *Staphylococcus aureus*. The peracid composition was processed in the supercritical fluid extraction system at a pressure of 200 bar and temperature of 80° C. for one hour, as described above in Examples 1–3 and with the following differences. The reaction chamber was periodically agitated manually during the processing. The antimicrobial was delivered to 10 mL of the microbial test solution (broth) by inserting the gas vent tube from a supercritical fluid extraction system into the solution, causing the antimicrobial vent gas to bubble through the solution. An aliquot of solution was removed at set time intervals and placed in an appropriate neutralizer to quench chemical activity. The solutions were then incubated and the reduction in the bacteria was determined. Exposure times of 30 seconds and two minutes were tested.

Results

As shown in Table 3, an exposure time of 30 seconds resulted in log reductions of 2.5 in the *S. aureus* population (experiment 1) and 1.1 in the *E. coli* population (experiment 2). An exposure time of two minutes resulted in log reductions of greater than 6 for both organisms.

TABLE 3

Antibacterial Efficacy in Solution Test

| | Bacteria Tested[1] | Log Reduction Collection Time | |
|---|---|---|---|
| | | 30 Seconds | 2 Minutes |
| 1 | *Staphylococcus aureus* ATCC 6538 | 2.5 | 6.3 |
| 2 | *Escherichia coli* ATCC 11229 | 1.1 | 6.1 |

[1]Antimicrobial gas (POAA in $CO_2$ gas) bubbled through 10 ml of bacteria solution.

Conclusion

Venting a densified fluid composition effectively delivers antimicrobial agents.

Example 5

Peroxyacetic Acid Antimicrobial Efficacy in Hard Surface Test

An antimicrobial agent produced in a densified fluid was tested for activity against microbes on a hard surface.

Material and Methods

The efficacy of peroxyacetic acid antimicrobial delivered via $CO_2$ gas was tested in a hard surface test against *Escherichia coli* and *Staphylococcus aureus*. The peroxyacetic acid antimicrobial was created by processing a peracid in-situ composition solution in the supercritical fluid extraction system at a pressure of 200 bar and temperature of 80° C. for one hour, generally as described in Examples 1–4 above.

A stainless steel coupon containing the bacteria was placed in a closed vessel (a syringe), and the antimicrobial was delivered into the vessel by inserting the gas vent tube from a supercritical fluid extraction system into the hole in the syringe. The coupons were exposed to the peroxyacetic acid antimicrobial vent gas for five minutes. Dry and wet methods were used for the testing. In the dry method, a dry film was generated on the coupon by adding a 20 µl suspension onto the coupon surface and drying the solution prior to the experiment. In the wet method, the 20 µl suspension was added to the coupon surface immediately before placing the coupon in the syringe and exposing it to the antimicrobial gas. After exposure to the antimicrobial gas for a set time period, the coupon was removed and placed in an appropriate neutralizer to stop the antimicrobial chemical activity. The bacteria remaining on the coupons were then incubated and the population reduction was determined.

Results

As shown in Table 4, log reductions of greater than five were obtained for all systems tested. The *S. aureus* bacteria (experiment 1) was found to have a log reduction of 5.5 for both the wet and dry methods. The *E. coli* (experiment 2) was found to have a log reduction of 6.5 for both methods.

TABLE 4

Antimicrobial Efficacy in Hard Surface Test

| | Bacteria Tested | Log Reduction | |
|---|---|---|---|
| | | Dry method[1] | Wet Method[2] |
| 1 | *Staphylococcus aureus* ATCC 6538 | 5.5 | 5.5 |
| 2 | *Escherichia coli* ATCC 11229 | 6.5 | 6.5 |

[1]Coupon containing dry bacterial film exposed to vent gas in closed vessel for five minutes.
[2]Coupon with 20 µl bacterial suspension exposed to vent gas in closed vessel for five minutes Conclusion Venting a densified fluid composition effectively delivers antimicrobial agents.

Example 7

Iodine Compound Antimicrobial Efficacy and Rate of Kill in Solution Test

The densified fluid system was tested for delivery of an iodine antimicrobial.

Materials and Methods

The efficacy of a quaternary interhalide (iodine releasing) antimicrobial (choline diiodo chloride) delivered via $CO_2$ gas was tested through an aqueous suspension test against *Escherichia coli*. The polyhalide composition preparation was processed in the supercritical fluid extraction system at a pressure of 200 bar and temperature of 80° C. (taking about 15 minutes) by procedures similar to those employed for peroxy acid agents. The other ingredients in the vessel included citric acid and sodium carbonate. The reaction chamber was periodically agitated manually during the processing. The polyhalide antimicrobial vent gas was then bubbled through 10 ml of the microbial broth. The antimicrobial was delivered to the microbial test solution (broth) by inserting the gas vent tube from a supercritical fluid extraction system into the solution, causing the antimicrobial vent gas to bubble through the solution. An aliquot of solution was removed at set time intervals and placed in an appropriate neutralizer to quench chemical activity. The solutions were then incubated and the reduction in the bacteria was determined. Exposure times of two and ten minutes were tested.

Results

As shown in Table 5, an exposure time of 2 minutes or greater resulted in log reductions of greater than 6-log in the *E. coli* population.

TABLE 5

Antibacterial Efficacy in Solution Test

| | Log Reduction Collection Time | |
|---|---|---|
| Bacteria Tested[1] | 2 minutes | 10 minutes |
| 1  *Escherichia coli* ATCC 11229 | 6.1 | 6.1 |

[1]Antimicrobial gas (polyhalide in $CO_2$ gas) bubbled through 10 ml of bacteria solution.

Conclusion

Venting a densified fluid composition effectively delivers antimicrobial agents.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "adapted and configured" describes a system, apparatus, or other structure that is constructed or configured to perform a particular task or adopt a particular configuration. The phrase "adapted and configured" can be used interchangeably with other similar phrases such as arranged and configured, constructed and arranged, adapted, constructed, manufactured and arranged, and the like.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. An antimicrobial composition comprising a densified fluid and an antimicrobial agent selected from the group consisting of a halogen antimicrobial agent, a peroxycarboxylic acid antimicrobial agent, a carboxylic acid antimicrobial agent, a phenolic antimicrobial agent, or a combination thereof, the antimicrobial agent being at least 0.01% by weight of the composition and soluble in the densified fluid.

2. The composition of claim 1, wherein the densified fluid comprises a near critical, critical, or supercritical fluid.

3. The composition of claim 1, wherein the fluid comprises carbon dioxide, water, xenon, argon, krypton, ammonia, methane, ethane, propane, methanol, isopropanol, or a mixture thereof.

4. The composition of claim 1, wherein the phenolic antimicrobial agent comprises phenol, BHT, mandelic acid, or salicylic acid, or a combination thereof.

5. The composition of claim 1, wherein the halogen antimicrobial agent comprises an interhalide, a polyhalide, a dibromodimethylhydantoin, chlorine, bromine, chlorine dioxide, hypochlorous acid, hypobromous acid, and mixtures thereof.

6. The composition of claim 5, further comprising an oxidizing agent.

7. The composition of claim 6, wherein the oxidizing agent comprises hydrogen peroxide, oxygen, ozone, or a mixture thereof.

8. The composition of claim 1, wherein the peroxycarboxylic acid antimicrobial agent comprises a peroxyacetic acid, a peroxyheptanoic acid, a peroxyoctanoic acid, a peroxynonanoic acid, peroxyformic acid, peroxycitric acid, peroxyglycolic acid, peroxylactic acid, or a combination thereof.

9. The composition of claim 8, further comprising an oxidizing agent and a carboxylic acid.

10. The composition of claim 9, wherein the carboxylic acid comprises acetic acid, butyric acid, heptanoic acid, octanoic acid, nonanoic acid, benzoic acid, lactic acid, glycolic acid, succinic acid, maleic acid, or a combination thereof.

11. The composition of claim 9, wherein the oxidizing agent comprises hydrogen peroxide, oxygen, ozone, or a mixture thereof.

12. The composition of claim 1, wherein the carboxylic acid antimicrobial agent comprises acetic acid, butyric acid, heptanoic acid, octanoic acid, nonanoic acid, benzoic acid, lactic acid, glycolic acid, succinic acid, maleic acid, or a combination thereof.

13. The composition of claim 1, wherein the densified fluid comprises carbon dioxide, the antimicrobial agent comprises peroxyacetic acid, and the composition further comprises hydrogen peroxide and acetic acid.

14. The composition of claim 13, comprising about 1 to about 20 parts acetic acid, about 0.1 to about 10 parts $H_2O_2$, and about 0.1 to about 20 parts peroxyacetic acid for each 10 to 10,000 parts of carbon dioxide.

15. The composition of claim 14, further comprising about 0.01 to about 0.9 parts phosphonate stabilizing agent and about 0.01 to about 100 parts deionized (DI) water for each about 10 to about 10,000 parts of carbon dioxide.

16. The composition of claim 15, wherein the phosphonate stabilizing agent is selected from the group consisting of 1-hydroxyethylidene-1,1-diphosphonic acid, amino (trimethylenephosphonic acid)) ($N[CH_2PO_3H_2]_3$), and ethylenediamine[tetra(methylenephosphonic acid)].

* * * * *